(12) United States Patent
Gellman et al.

(10) Patent No.: US 9,556,217 B2
(45) Date of Patent: Jan. 31, 2017

(54) AMPHIPHILIC COMPOUNDS

(71) Applicants: WISCONSIN ALUMNI RESEARCH FOUNDATION, Madison, WI (US); The Board of Trustees of the Leland Stanford Junior University, Palo Alto, CA (US)

(72) Inventors: Samuel Helmer Gellman, Madison, WI (US); Pil Seok Chae, Ansan-Si (KR); Brian Kobilka, Palo Alto, CA (US); Soren Rasmussen, Gentofte (DK)

(73) Assignees: Wisconsin Alumni Research Foundation, Madison, WI (US); The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/931,225

(22) Filed: Nov. 3, 2015

(65) Prior Publication Data

US 2016/0060290 A1     Mar. 3, 2016

Related U.S. Application Data

(63) Continuation of application No. 13/826,466, filed on Mar. 14, 2013, now Pat. No. 9,206,221.

(60) Provisional application No. 61/621,293, filed on Apr. 6, 2012.

(51) Int. Cl.
```
C07J 17/00      (2006.01)
C07J 41/00      (2006.01)
A61K 9/107      (2006.01)
C07J 71/00      (2006.01)
```

(52) U.S. Cl.
CPC ............ C07J 17/005 (2013.01); A61K 9/1075 (2013.01); C07J 41/0061 (2013.01); C07J 71/0005 (2013.01)

(58) Field of Classification Search
CPC ... C07J 17/005; C07J 71/0005; C07J 41/0061; A61K 9/1075
USPC .................. 252/181.12; 530/350, 422; 536/5
See application file for complete search history.

(56) References Cited

U.S. PATENT DOCUMENTS

| | | | | |
|---|---|---|---|---|
| 7,635,695 B2 * | 12/2009 | Burkitt | ................. | C07D 231/56 514/233.8 |
| 8,263,754 B2 * | 9/2012 | Gellman | ................ | C07H 15/02 530/409 |
| 8,815,263 B2 * | 8/2014 | Chae | .................... | C07J 41/0061 424/400 |
| 8,877,906 B2 * | 11/2014 | Gellman | ................ | C07H 15/02 530/409 |
| 9,206,221 B2 * | 12/2015 | Gellman | ................ | C07J 17/005 |
| 2006/0148021 A1 | 7/2006 | Herbert | | |
| 2009/0270598 A1 * | 10/2009 | Gellman | ................ | C07H 15/02 530/409 |
| 2010/0311956 A1 | 12/2010 | Gellman et al. | | |
| 2013/0001465 A1 * | 1/2013 | Gellman | ................ | C07H 15/02 252/182.12 |
| 2013/0266656 A1 * | 10/2013 | Gellman | ................ | C07J 17/005 424/490 |
| 2013/0324707 A1 * | 12/2013 | Gellman | ................ | C07H 15/26 530/412 |
| 2015/0011739 A1 * | 1/2015 | Chae | .................... | C07J 41/0061 536/5 |

OTHER PUBLICATIONS

Boullanger et al. (Chemistry and Physics of Lipids 87 (1997) 91-101).
Chae et al., "Maltose-neopentyl glycol (MNG) amphiphiles for solubilization, stabilization and crystallization of membrane proteins," Nature America, Inc., Dec. 2010, 7, 12:1003-1008.
Chae et al., "Tandem Facial Amphiphiles for Membrane Protein Stabilization," JACS Communications, 2010, 132(47):16750-16752.
Cheng et al., "Facial Amphiphiles," J. Am. Chem. Soc., 1992, 114(18): 7319-7320.
Chierici et al., "Synthesis and interfacial behaviour of a gemini neoglycolipid," Chemistry and Physics of Lipids, 1997, 87:91-101.
Dumoulin et al., "Synthesis and Liquid Crystalline Properties of Mono- Di- and Tri-O-alkyl Pentaerythritol Derivatives Bearing Tri-, Di- or Monogalactosyl Heads: The Effects of Curvature of Molecular Packing on Mesophase Formation," Chem. Eur. J., 2007, 13:5585-5600.
Hjelmeland, "The Design and Synthesis of Detergents for Membrane Biochemistry," Methods in Enzymology, 1986, vol. 124:135-164.
Hovers et al., "A class of mild surfactants that keep integral membrane proteins water-soluble for functional studies and crystallization," Molecular Biology, 2011, 28(3): 171-181.
Kim et al., "Synthesis of New Building Blocks for Boron-Rich Oligomers in Boron Neutron Capture Therapy (BNCT). II. Monomers Derived From 2,2-Disubstituted-1,3-Diols," Tetrahedron Letters, 1995, 36(29):5147-5150.
McGregor et al., "Lipopeptide detergents designed for the structural study of membrane proteins," Nature Publishing Group, 2003, 21:171-176.

(Continued)

Primary Examiner — Sabiha N Qazi
(74) Attorney, Agent, or Firm — Joseph T. Leone, Esq.; DeWitt Ross & Stevens S.C.

(57) ABSTRACT

Bringing membrane proteins into aqueous solution generally requires the use of detergents or other amphiphilic agents. The invention provides a new class of amphiphiles, each of which includes a multi-fused ring system as a lipophilic group. These new amphiphiles confer enhanced stability to a range of membrane proteins in solution relative to conventional detergents, leading to improved structural and functional stability of membrane proteins, including integral membrane proteins. Accordingly, the invention provides new amphiphiles for biochemical manipulations and characterization of membrane proteins. These amphiphiles display favorable behavior with membrane proteins and can be used to aid the solubilization, isolation, purification, stabilization, crystallization, and/or structural determination of membrane proteins.

18 Claims, 15 Drawing Sheets

(56) References Cited

OTHER PUBLICATIONS

Privé, "Detergents for the stabilization and crystallization of membrane proteins," *Methods*, 2007, 41:388-397.
Rasmussen et al., "Crystal Structure of the β2 Adrenergic Receptor-Gs protein complex," *Nature*, 2012, 477 (7366): 549-555.
Rasmussen et al., "Structure of a nanobody-stabilized active state of the β2 adrenocepter," *Nature*, 2011, 469: 175-179.
Rosenbaum et al., "Structure and function of an irreversible agonist-β2 adrenocepter Complex," *Nature*, 2011, 469: 236-240.
Schafmeister et al., "Structure at 2.5 A of a Designed Peptide That Maintains Solubility of Membrane Proteins," *Science*, 1993, 262: 734-738.
Silverman, "The Organic Chemistry of Drug Design and Drug Action," *Northwestern University Department of Chemistry*, 1992, 19-23.
Zhang et al., "Designing Facial Amphiphiles for the Stabilization of Integral Membrane Proteins," *Angewandte Chemie*, 2007, 46: 7023-7025.

\* cited by examiner

AMPHIPHILIC COMPOUNDS

RELATED APPLICATIONS

This is a continuation of co-pending application Ser. No. 13/826,466, filed Mar. 14, 2013, which claims priority under 35 U.S.C. §119(e) to provisional application Ser. No. 61/621,293, filed Apr. 6, 2012, which is incorporated herein by reference.

GOVERNMENT SUPPORT

This invention was made with government support under GM075913, GM083118, and NS028471 awarded by the National Institutes of Health. The government has certain rights in the invention.

BACKGROUND OF THE INVENTION

Integral membrane proteins (IMPs) are crucial cellular components, mediating the transfer of material and signals between the extracellular environment and the cytoplasm, or between different cellular compartments. Structural and functional analysis of IMPs is important to furthering our understanding of membrane protein interactions. More than half of current pharmaceutical agents target proteins in this class. IMP characterization is often challenging, and sometimes impossible, because of difficulties associated with handling these macromolecules. IMPs in the native state display large hydrophobic surfaces, which are not compatible with an aqueous environment. Detergents are therefore required to extract IMPs from the lipid bilayer and to maintain the native state of the protein in solution. Nonionic detergents, such as dodecyl-β-D-maltoside (DDM) and octyl-β-D-glucoside (OG), are commonly used for these extractions. Despite the comparatively mild nature of DDM, OG and related detergents, many membrane proteins denature and/or aggregate upon solubilization with these agents.

Diverse strategies have been pursued to develop new tools for solubilization of IMPs from membranes and for maintenance of these proteins in a native-like state in aqueous solution. Unfortunately, techniques that are effective for solubilization are not always optimal or effective for stabilization, and vice versa. Strategies for developing new IMP tools have included exploration of small amphiphilic molecules that depart from traditional detergent architectures. Small amphiphiles that facilitate IMP crystallization are particularly noteworthy (see Chae et al., *Nat. Methods* 2010, 7, 1003-1008; Hovers et al., *Mol. Membr. Biol.* 2011, 28, 170; Rasmussen, et al., *Nature* 2011, 469, 236-240; Rosenbaum et al., *Nature* 2011, 469, 175-180; Rasmussen et al., *Nature* 2011, doi: 10.1038/nature10361).

Amphiphilic polymers ("amphipols") and discoidal lipid bilayers stabilized by an amphiphilic protein scaffold ("nanodiscs") represent highly innovative approaches for stabilizing IMPs in native-like states in aqueous solution. It is not clear, however, whether either of these approaches can support growth of high-quality crystals for diffraction analysis. Furthermore, neither amphipols nor nanodiscs were designed to extract IMPs from biological membranes. Despite considerable progress in the development of new compounds and strategies for membrane protein solubilization and stabilization, new tools are needed, because many IMPs are currently refractory. Given the great variation in structure and physical properties among membrane proteins, it is very unlikely that a single amphiphile or amphiphile family will be optimal for every system, or even most systems.

Accordingly, there is a need for new classes of structurally novel amphiphiles that display favorable behavior, relative to traditional detergents such as DDM, toward a diverse set of membrane proteins. There is also a need for novel amphiphiles that can aid membrane protein manipulation techniques such as solubilization, isolation, stabilization, and crystallization.

SUMMARY

The invention provides new amphiphiles for protein manipulation. The manipulation can include solubilization, stabilization, isolation, purification, crystallization and/or assistance in structural determination of membrane proteins, such as difficult to solubilize integral membrane proteins. The new class of amphiphiles can bear rigid hydrophobic groups derived from steroid-like structures for manipulation of membrane proteins.

The invention thus provides a compound of Formula I:

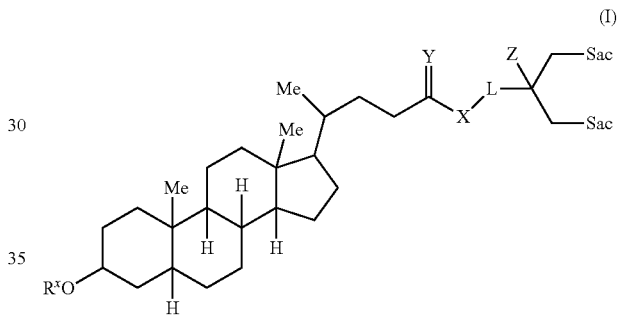

wherein

L is —(CH$_2$)$_n$— where n is 1-12, or a direct bond;

X is NH, O, or a direct bond;

Y is O or absent;

Z is H, methyl, ethyl, propyl, or butyl;

R$^x$ is H, optionally substituted (C$_1$-C$_{24}$)alkyl, optionally substituted aryl or aroyl, or an oxygen-linked monosaccharide, disaccharide, or trisaccharide; and each Sac is independently an oxygen-linked monosaccharide, disaccharide, or trisaccharide.

The variable R$^x$ can be methyl, ethyl, propyl, or any optionally substituted (C$_1$-C$_{24}$)alkyl group. Each Sac can be an oxygen-linked monosaccharide, an oxygen-linked disaccharide, or an oxygen-linked trisaccharide. Various specific saccharides that can be attached to Formula I include those recited herein in the definition of saccharide. In some embodiments, each Sac group is a disaccharide moiety, such as a maltosyl group.

In some embodiments, X is NH, Y is O, Z is H, and L is a direct bond.

In other embodiments, L is —CH$_2$—, X is O, Y is absent, and Z is Me.

In yet other embodiments, L is a direct bond, X is a direct bond, Y is absent, and Z is H.

The compound of Formula I can be a compound of Formula II, III, or IV:

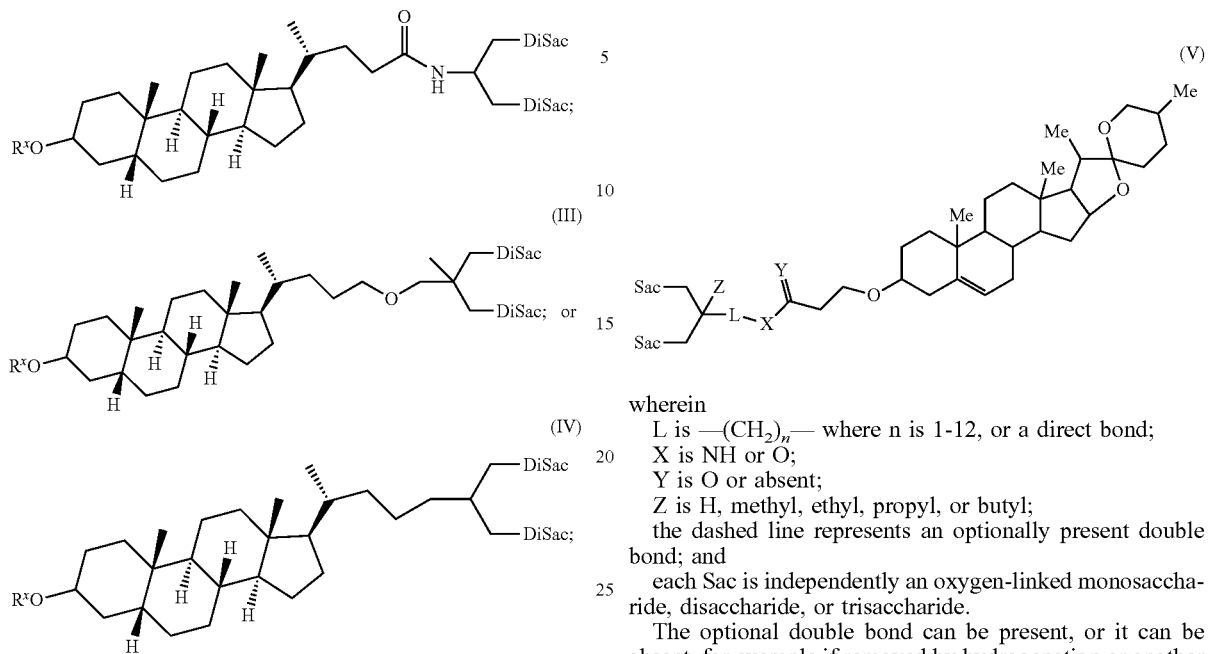

wherein DiSac is an oxygen-linked disaccharide. In certain specific embodiments, the compound is:

In another embodiment, the invention provides a compound of Formula V:

wherein
L is —(CH$_2$)$_n$— where n is 1-12, or a direct bond;
X is NH or O;
Y is O or absent;
Z is H, methyl, ethyl, propyl, or butyl;
the dashed line represents an optionally present double bond; and
each Sac is independently an oxygen-linked monosaccharide, disaccharide, or trisaccharide.

The optional double bond can be present, or it can be absent, for example if removed by hydrogenation or another reduction reaction.

Each Sac can be an oxygen-linked monosaccharide, an oxygen-linked disaccharide, or an oxygen-linked trisaccha-

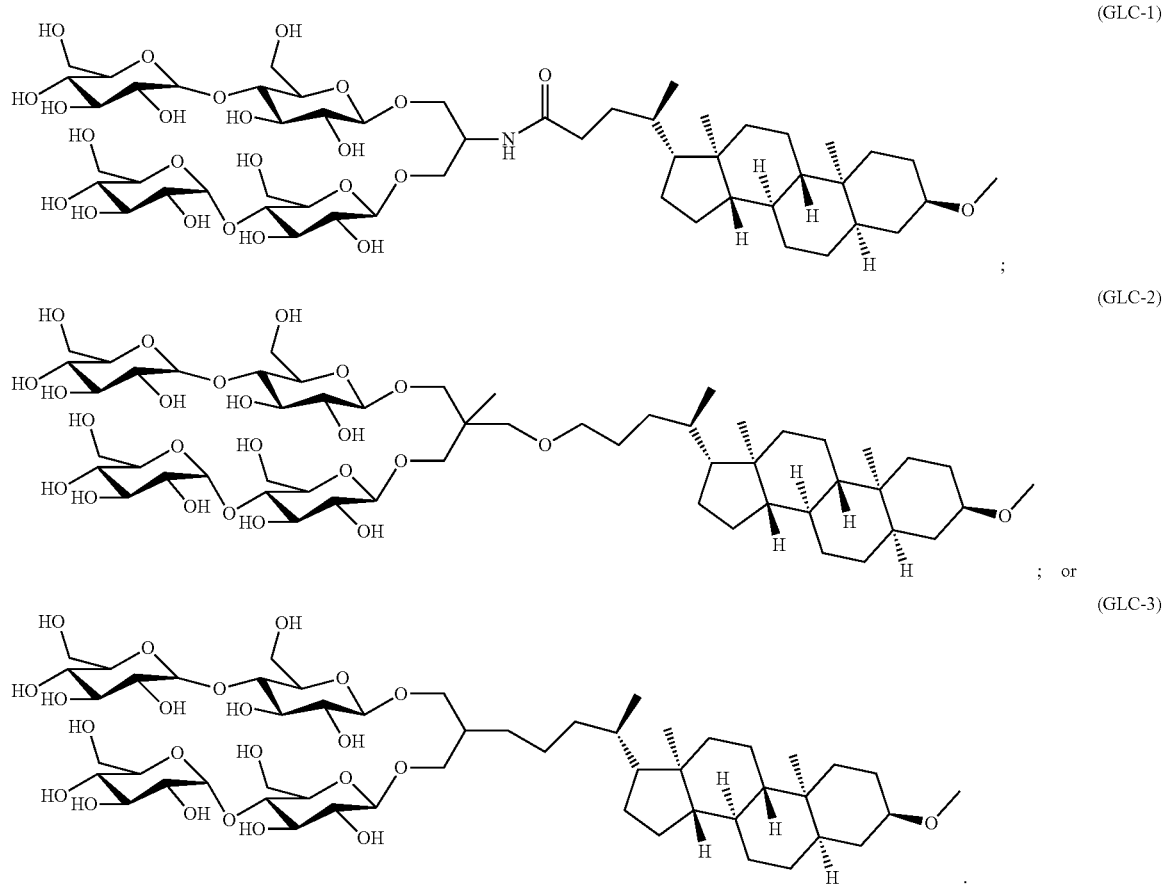

ride. Various specific saccharides that can be attached to Formula I include those recited herein in the definition of saccharide. In some embodiments, each Sac group is a disaccharide moiety, such as a maltosyl group.

In some embodiments, X is NH, Y is O, Z is H, and L is a direct bond.

In other embodiment, L is —CH$_2$—, X is O, Y is absent, and Z is Me.

In yet other embodiments, L is a direct bond, X is a direct bond, Y is absent, and Z is H.

In further embodiments, the variable n of group L can be 1, 2, 3, 4, 5, 6, 7, 8, 9, 10, 11, or 12, for example, for either Formula I or Formula V.

The compound of Formula V can be a compound of Formula VI:

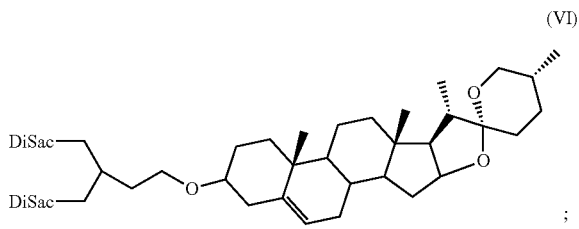

(VI)

wherein DiSac is an oxygen-linked disaccharide.

The compound of Formula VI can be, for example:

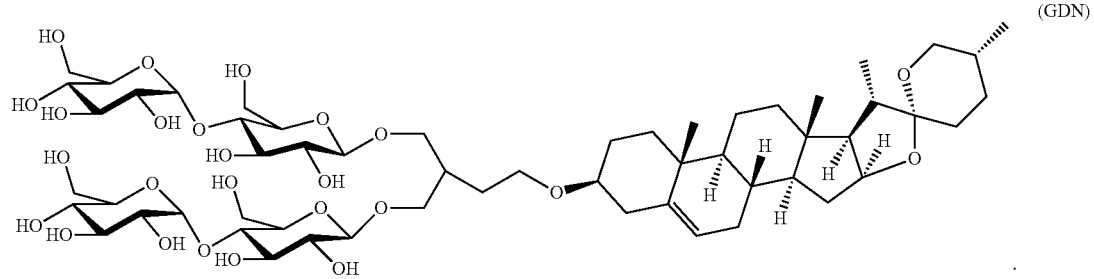

(GDN)

The stereochemistry of the above formulas and structures are merely illustrative of certain embodiments. The invention can include other stereoisomers including the enantiomers and various diastereomers of the formulas and structures shown.

In some embodiments, the critical micelle concentration (CMC) of a compound of Formula I-VI in water is about 5 nM to about 100 nM. In various embodiments, the CMC can be about 5 nM to about 60 nM, about 5 nM to about 20 nM, or about 45 nM to about 55 nM. A plurality of the compounds can form a micelle in water comprising about 5 to about 35 molecules of the compound. Some micelles can include about 5 to about 10, about 10 to about 15, about 5 to about 20, about 5 to about 15, about 10 to about 20, or about 5 to about 25 molecules of the compound in the formation of individual micelles.

The invention also provides a composition comprising a plurality of compounds as described above and an isolated membrane protein. The composition can include micelles that include the compounds described herein encapsulating the isolated membrane protein, optionally in combination with other compounds, amphiphiles, or surfactants in the micelle structure. The micelle can optionally include one or more drugs, therapeutic molecules, bioactive molecules, polypeptides, proteins, genes, or a combination thereof, within the micelle. In some embodiments, the molecule within the micelle is a polypeptide or a protein.

The invention also provides methods of solubilizing or stabilizing a membrane protein comprising contacting a membrane protein with an effective amount of a plurality of compounds described herein, in an aqueous solution. The methods can and optionally include heating the protein and the compounds, thereby forming a solubilized or stabilized aggregation or micelle of the compounds and the membrane protein. The invention further provides methods of extracting a protein from a lipid bilayer comprising contacting the lipid bilayer with an effective amount a plurality of compounds described herein in an aqueous solution or suspension to form a mixture, optionally in the presence of a buffer, thereby forming an aggregation or micelle of the compounds and the membrane protein that has been extracted from the lipid bilayer. The aggregates and/or micelles can then be separated from the mixture to provide the isolated proteins. The compounds described herein can be particularly valuable for stabilizing proteins in a functional form such that the protein can be analyzed by various assays, such as a ligand binding assay.

The invention therefore provides novel compounds and formulas, intermediates for the synthesis of the compounds and formulas, as well as methods of preparing the compounds, formulas, and compositions described herein. The invention also provides compounds that are useful as intermediates for the synthesis of other valuable compounds. The invention further provides methods of using the compounds, for example, to aid the solubilization, isolation, purification, stabilization, crystallization, and/or structural determination of membrane proteins. The compounds of the invention can be used alone, or in combination with lipids or known detergents. Other objects, features and advantages of the present invention will become apparent from the following description, claims and drawings.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
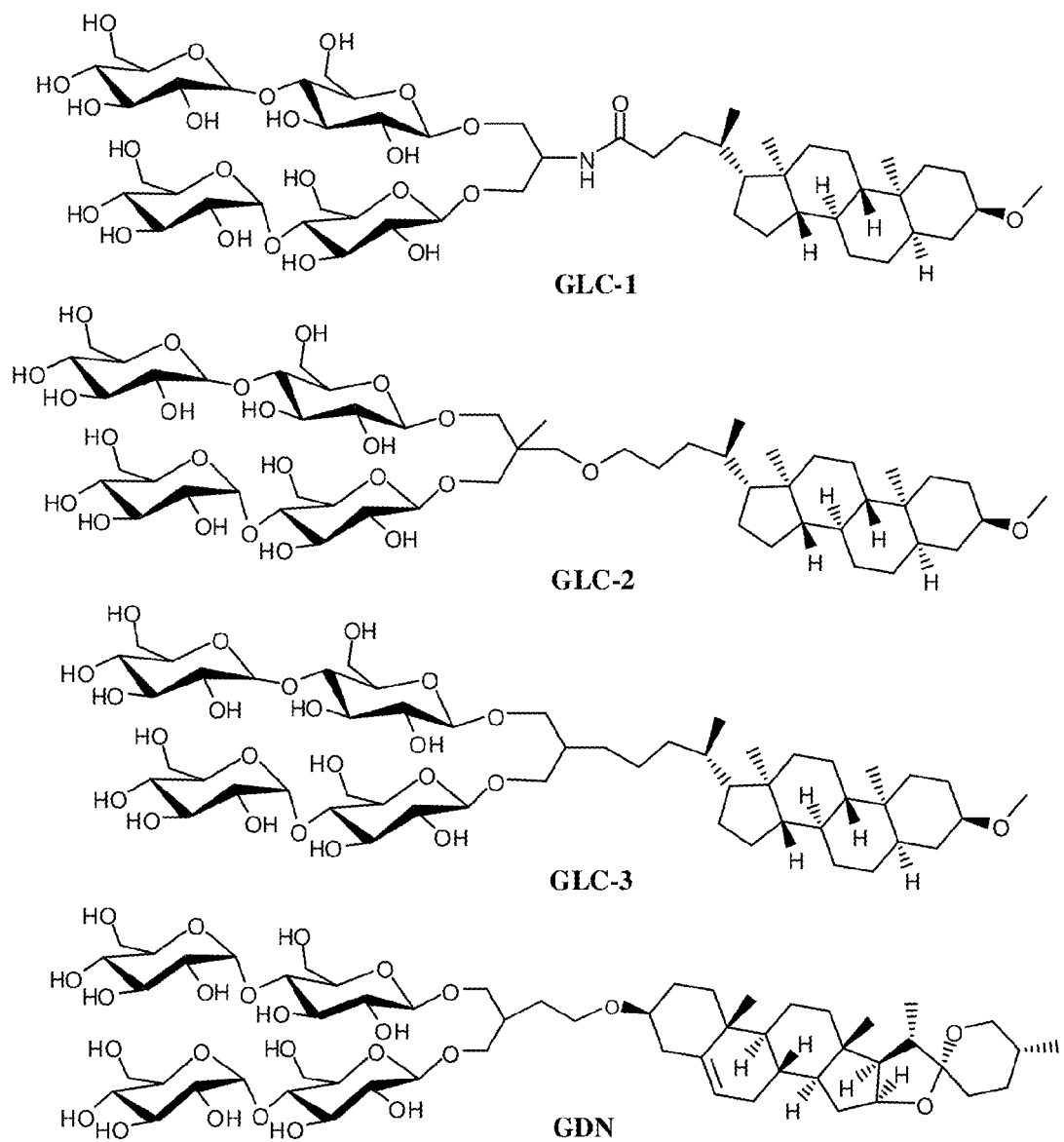
FIG. 1. Chemical structures of new amphiphiles GLC-1, GLC-2, GLC-3, and GDN.

The difficulty of obtaining crystal structures for membrane proteins represents a profound hindrance to fundamental and applied biological research. Many MPs cannot be maintained in native-like conformations when solubilized with conventional detergents. Moreover, even when a native conformation can be achieved, the MP-detergent complex with traditional detergents such as DDM can manifest unfavorable properties with regard to structural analysis. The complexes may have the inability to crystallize, and/or the complexes formed may be too large for effective NMR analysis). Because our understanding of membrane protein structure and function remains poorly developed relative to soluble proteins, there is a persistent need for new amphiphilic "assistants" that can promote solubilization and manipulation of MPs.

Bringing membrane proteins into aqueous solution generally requires the use of a detergent or other amphiphilic agents. Disclosed herein is a new class of amphiphiles, each of which uses a multi-fused ring system as a lipophilic group. This family of molecules confers enhanced stability to a range of membrane proteins in solution relative to conventional detergents, leading to improved structural and functional stability of integral membrane proteins (IMPs).

Analyses of the new amphiphiles indicate they are comparable or superior to the commonly used biochemical detergent DDM with respect to several different protein systems. These results indicate that the new amphiphiles are at least complementary to current technology, such as known commercial biochemical detergents, in the context of many membrane proteins that researchers would like to study. In general, a significant fraction of these proteins of interest remain very difficult to examine, and so new amphiphiles with distinctive structures and properties, such as those described herein, will be attractive as research tools.

A large number of amphiphiles are needed on the market for characterization and solubilization work, because many alternatives must be tried for each membrane protein to identify the best match. Accordingly, the amphiphiles described herein will provide additional resources to researchers for manipulating membrane proteins. For example, the amphiphiles can be used as reagents for protein solubilization and crystallization, especially for generally insoluble proteins. The amphiphiles can also be used as reagents for protein stabilization, so that the proteins can be analyzed by various ligand binding assays. For a continuously updated database of MP structures, each of which can be potentially suitably manipulated by the amphiphiles described herein, see: http://blanco.biomol.uci.edu/Membrane_Proteins_xtal.html.

Before the amphiphiles and methods are further described, it is noted that this invention is not limited to the particular methodology, protocols, materials, and reagents described, as these may vary. For example, various sugars, disaccharides and trisaccharides can be exchanged for other isomers in the preparation of the compounds. It is also to be understood that the terminology used herein is for the purpose of describing particular embodiments only and is not intended to limit the scope of the invention, which is limited only by the appended claims.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The phrase "treating a protein" with a compound, detergent, surfactant, or "agent" refers to contacting the protein with the agent (e.g., an amphiphile as described herein), and/or combining the protein with an effective amount of the agent under conditions that allow the agent to penetrate, integrate and/or disrupt a protein's current environment in order to solubilize, stabilize, isolate, and/or purify the protein. The conditions can be aqueous and additional reagents, such as buffers, salts, and the like, can be added. The treating can use a single type of agent, such as an amphiphile described herein, or the treating can employ a combination of agents, such as an amphiphile described herein in combination with one or more surfactants such as DDM, CHAPS, CHAPSO, and the like. Thus, a combination of reagents may be employed in the treatment. The protein may be, for example, in a lipid bilayer or substantially isolated in solution.

Detergent-solubilized membrane proteins are typically more thermolabile than their membrane-embedded forms, therefore stabilizing a protein is important for research and analysis. The phrase "stabilizing a protein" refers to treating a protein so that the protein thermostability improves, or so that the protein retains activity (e.g., of a particular receptor), or maintains a native confirmation, for example, when extracted from a membrane. Stabilizing a membrane protein with an amphiphile as described herein can be, for example, improving its T50 value by about 5° C., about 10° C., about 15° C., about 20° C., or about 25° C., for example, compared to a standard detergent such as DDM. Increasing the stability of an isolated protein is important to allow researchers sufficient time to examine and characterize the protein.

Methods of the invention include treating a protein, for example, using such techniques as solubilization, isolation, purification, stabilization, crystallization, and/or structural determination. The methods can include standard laboratory techniques such as lysing a cell, precipitation, concentration, filtration, and/or fractionation.

An "effective amount" refers to an amount effective to bring about a recited effect. For example, an amount effective can be an amount of an agent or combination of reagents effective to solubilize or stabilize a membrane protein.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be a monovalent hydrocarbon radical, as described and exemplified above, or it can be a divalent hydrocarbon radical (i.e., an alkylene), according to the context of its usage. The term "aroyl" refers to the group aryl-C(=O)—. Examples of aryl groups include benzyl, anthryl, biphenyl, and the like. The aryl groups of the aroyl can be optionally substituted with substituents such as alkyl, halo (F, Cl, Br, or I), nitro, amino, and the like.

The term "saccharide" refers to a sugar or sugar moiety, such as a monosaccharide, a disaccharide, or a trisaccharide. Typical monosaccharides include allose, altrose, glucose, mannose, gulose, idose, galactose, or talose. Typical disaccharides include galactose, lactose, maltose, sucrose, trehalose, and cellobiose. Disaccharides can have any suitable linkage between the first and the second unit of the disaccharide. Other suitable saccharides include glucuronic acid, sorbase, ribose, and the like. A saccharide can include hydroxyl protecting groups such as, but not limited to, acetyl groups, benzyl groups, benzylidene groups, silyl groups, methoxy ether groups, or combinations thereof. The saccharide groups can also be in pyranose form, furanose form, or linear form. The saccharides can be linked to Formula described herein via their anomeric oxygen, or to any other available hydroxyl group. Depending on the context, as would be understood by one of skill in the art, the saccharide can include the oxygen that links it to another group, or exclude the oxygen that links it to another group.

Trisaccharides are oligosaccharides composed of three monosaccharides with two glycosidic bonds connecting them. Similar to disaccharides, each glycosidic bond can be formed between any hydroxyl group on the component monosaccharides. The three monosaccharide components can have different bond combinations (regiochemistry) and stereochemistry (alpha- or beta-linkages) to provide trisaccharides that are various diastereomers. Examples of trisaccharides include nigerotriose, maltotriose, maltotriulose, and raffinose.

The saccharides described herein may include one or more hydroxyl protecting groups, such as benzyl groups, acetyl groups, or benzoyl groups. However, some embodiments have most or all of the protecting groups removed from the saccharide groups of the amphiphiles described herein.

The "Critical Micelle Concentration" (CMC) refers to the concentration of a detergent (e.g., an amphiphile as described herein) in an aqueous solution at which the detergent molecules self-assemble into micelles. Below the CMC, detergents are mostly monomeric; above the CMC, micelle concentration increases linearly with detergent concentration. The CMC is dependent upon many factors and is detergent-specific. The CMC of a detergent can be determined experimentally by measuring the solubilization of a water-insoluble dye or fluorophore while varying the concentration of detergent. A CMC may also be determined by measuring the diminution of the surface tension of an aqueous solution as a function of detergent concentration (CMCs determined by either method correlate with each other). The CMC is determined by extrapolating the plot of solubilization vs. concentration (or surface tension vs. concentration) in the two linear regions above and below the CMC. Where the two lines intersect is the CMC. The CMC can also be determined by the method of Nugebauer, J. M. (1990), Methods in Enzymology, 182:239-253.

Amphiphiles for Membrane Protein Manipulation

The new amphiphiles can contain a rigid, steroid-based lipophilic group and a pair of saccharides to provide a hydrophilic group. Four specific examples are illustrated in FIG. 1. Three of the new compounds are derived from lithocholic acid and are therefore designated "glyco-lithocholate" amphiphiles (GLC-1, GLC-2 and GLC-3); the fourth is derived from diosgenin and is designated "glyco-diosgenin" (GDN). Previously reported amphiphiles based on steroidal skeletons have been derivatives of cholic acid or deoxycholic acid, including members of the widely-used CHAPS family, cholate-based facial amphiphiles, and tandem-facial amphiphiles (Hjelmeland, *Proc. Natl. Acad. Sci. USA* 1980, 77, 6368-6370; Zhang et al., *Angew. Chem. Int. Ed.* 2007, 46, 7023-7025; Chae et al., *J. Am. Chem. Soc.* 2010, 132, 16750-16752). In these cases the rigid steriodal units are facially amphiphilic: one side is hydrophilic, displaying either hydroxyl groups or carbohydrate units. In contrast, the hydrophobic units in the GLC and GDN amphiphiles introduced here are hydrophobic on both faces, and the hydrophilic moiety is appended to the periphery of the rigid hydrophobic unit.

The four compounds were readily prepared on a multi-gram scale (see Examples 1 and 2 below, and FIGS. 13-15), as is necessary if they are to serve as research tools. All four are highly soluble in aqueous solution (>20 wt %) and have relatively low critical micelle concentrations (CMC; determined by fluorescent dye solubilization). See Table 1.

TABLE 1

Critical Micelle Concentration (CMC) of GLC/GDN amphiphiles and hydrodynamic radii (Rh) of their micelles (Mean ± SD, n = 5).

|  | MW[a] | CMC (μM) | CMC (wt %) | $R_h$ (nm)[b] |
|---|---|---|---|---|
| GLC-1 | 1112.3 | ~52 | ~0.006 | 3.22 ± 0.03 |
| GLC-2 | 1127.3 | ~8.0 | ~0.0009 | 3.32 ± 0.04 |
| GLC-3 | 1083.3 | ~7.1 | ~0.00077 | 3.27 ± 0.04 |
| GDN | 1165.3 | ~18 | ~0.0021 | 3.86 ± 0.05 |
| DDM | 510.1 | ~170 | ~0.0087 | 3.42 ± 0.03 |

[a]Molecular weight of detergents.
[b]Hydrodynamic radius of micelles measured by dynamic light scattering.

These values are somewhat smaller than the CMC of DDM, which indicates a strong tendency of the new agents to self-assemble, and which can be advantageous for IMP handling because detrimental levels of non-micellar amphiphile can be avoided. Table 1 provides the hydrodynamic radius (Rh) of the micelles formed by each amphiphile, as determined by dynamic light scattering (DLS). The micelles formed by GLC amphiphiles are slightly smaller than those formed by DDM, while the micelles formed by GDN are slightly larger.

Thus, the amphiphiles described herein can be prepared from commercially available steroidal precursors such as cholesterol and related molecules. The steroid precursor compound can be rendered water-soluble by attachment of a bis-saccharide unit, such as a bis-maltoside unit. The amphiphiles generally fall into two classes, GLCs and GDNs (see FIG. 1). These amphiphilic molecules can be used as tools in biochemistry, specifically for solubilization, stabilization and crystallization of membrane proteins.

Figure 13:
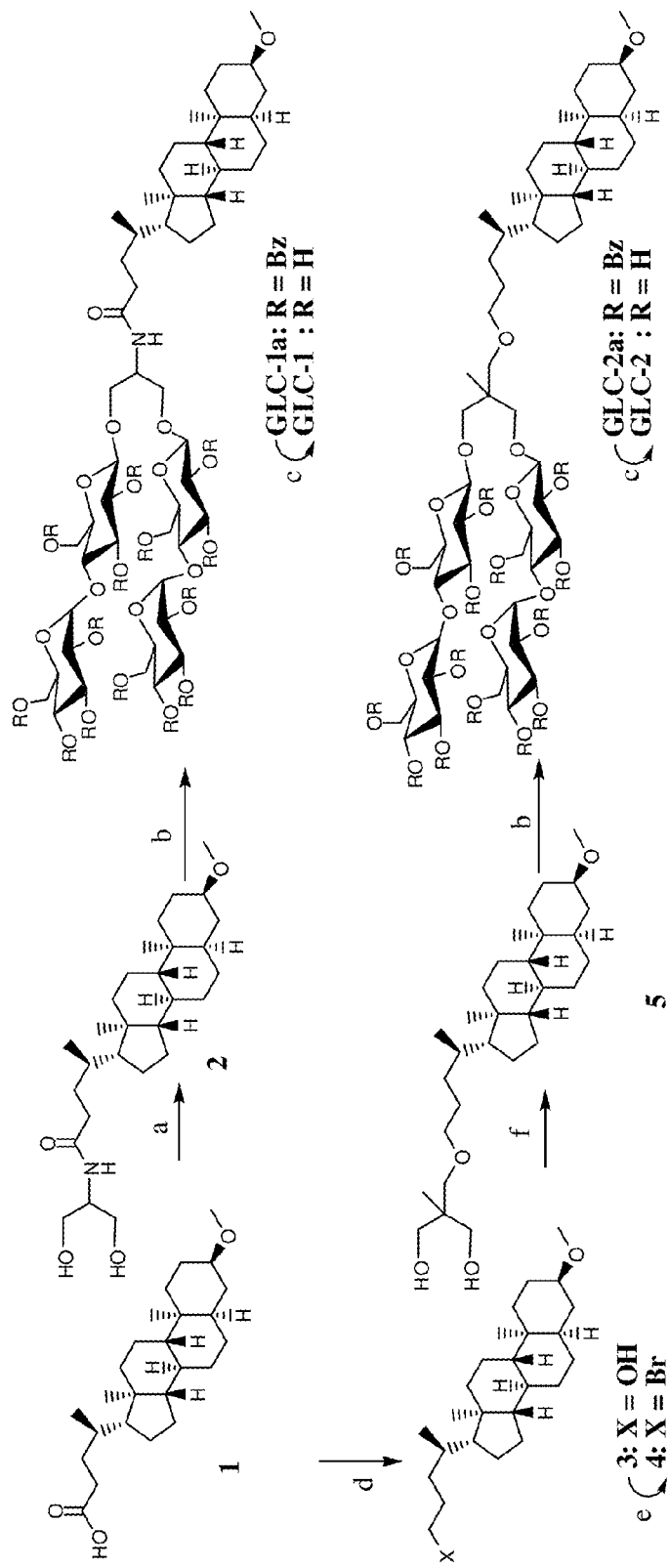
FIG. 13. Synthetic scheme for the preparation of GLC-1 and GLC-2. Reagents and conditions: (a) EDC.HCl, HOBt, DMF, RT, 2 days; (b) perbenzoylated maltosylbromide, AgOTf, $CH_2Cl_2$, −45° C.→RT, 3 hr; (c) NaOMe, MeOH, RT, 4 hr; (d) $LiAlH_4$, THF, RT, 1 day; (e) $CBr_4$, $Ph_3P$, MeCN:THF, RT, 15 hr; (f) 1,1,1-Tris(hydroxymethyl)ethane, NaH, 60° C., 2 hr.
Figure 14:
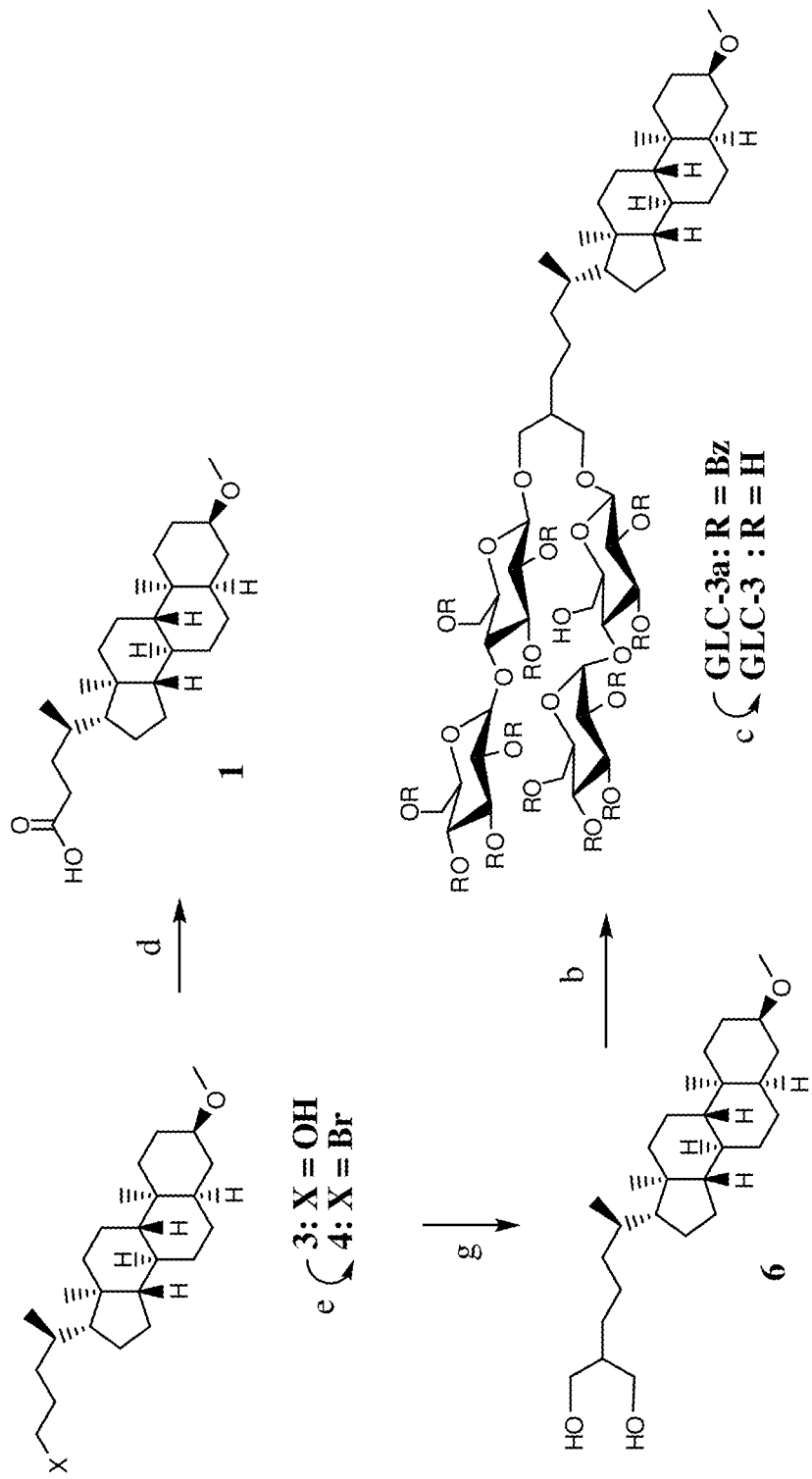
FIG. 14. Synthetic scheme for the preparation of GLC-3. Reagents and conditions: (b) perbenzoylated maltosylbromide, AgOTf, $CH_2Cl_2$, −45° C.→RT, 3 hr; (c) NaOMe, MeOH, RT, 4 hr; (d) $LiAlH_4$, THF, RT, 1 day; (e) $CBr_4$, $Ph_3P$, MeCN:THF, RT, 15 hr; (g) diethylmalonate, NaH, THF, RT, 15 hr; $LiAlH_4$, THF, RT, 1 day.
Figure 15:
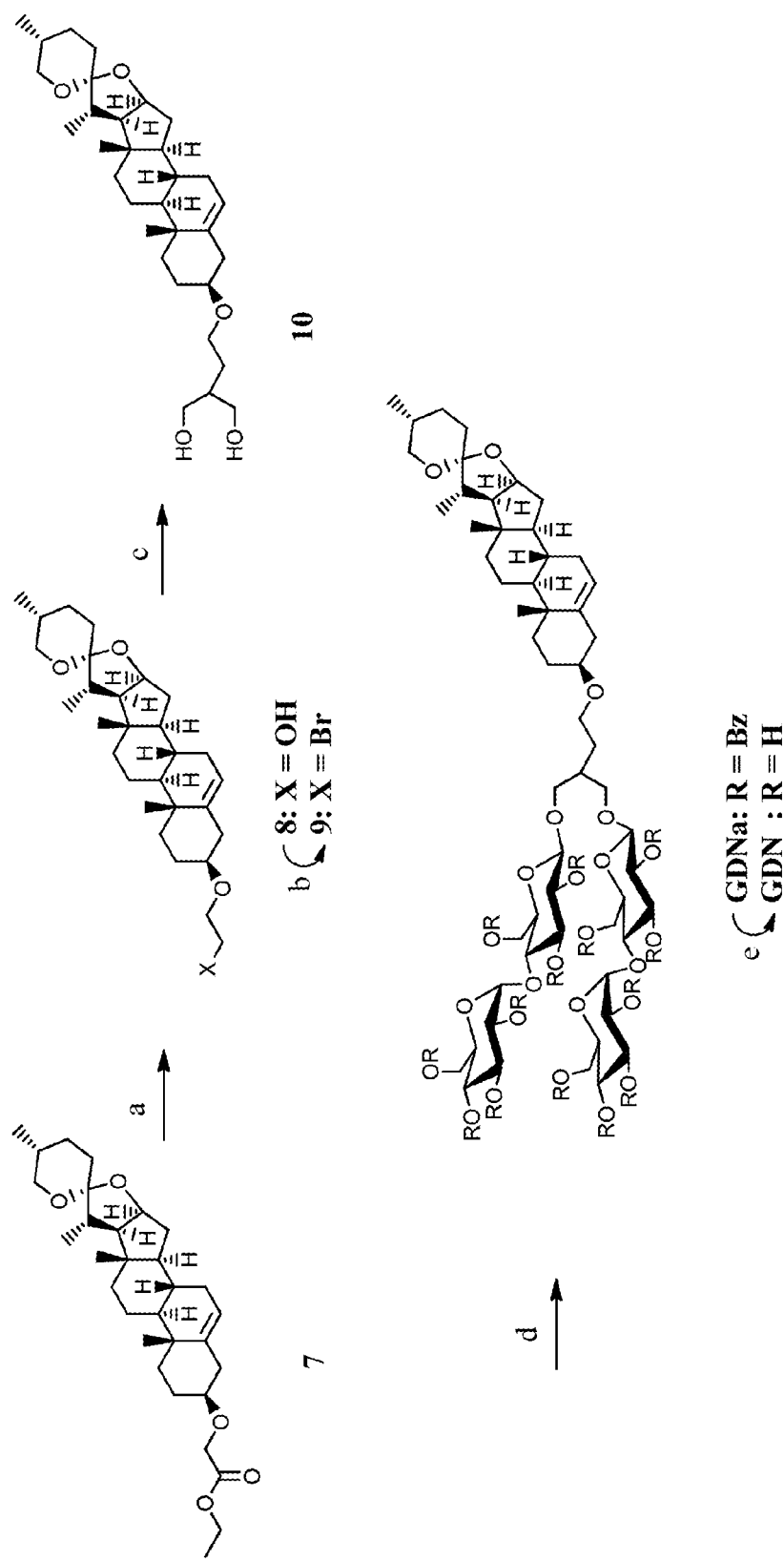
FIG. 15. Synthetic scheme for the preparation of the amphiphile GDN. Reagents and conditions: (a) $LiAlH_4$, THF, RT, 1 day; (b) $CBr_4$, $Ph_3P$, $CH_2Cl_2$, RT, 15 hr; (c) diethylmalonate, NaH, THF, RT, 1 day; $LiAlH_4$, THF, RT, 1 day; (d) perbenzoylated maltosylbromide, AgOTf, $CH_2Cl_2$, −45° C.→RT, 3 hr; (e) NaOMe, MeOH, RT, 4 hr.

For example, amphiphiles can be prepared as illustrated in FIGS. 13-15. The acid functionality of lithocholic acid can be converted to an amide, ether, or alkylene linking group, which can then be glycosylated with various saccharides, such as maltosyl groups, or other saccharides recited herein. In other embodiments, the free hydroxyl of diosgenin can be functionalized similarly with ether, or alkylene linking group, which can also be glycosylated as described herein. The protected saccharide groups can then be deprotected or partially deprotected to provide various amphiphiles of the invention.

The saccharide moieties can be maltose, as illustrated in FIGS. 13-15, or they can be other saccharides, such as one or more of the monosaccharides, disaccharides, or trisaccharides recited herein. The saccharides can include various protecting groups, as would be well understood by one of skill in the art. Specific protecting groups include benzyl, acetyl, trifluoroacetyl, benzoyl, benzyloxycarbonyl, and silicon protecting groups such as trimethylsilyl, t-butyldimethylsilyl, and diphenylmethylsilyl. Other suitable protecting groups are known to those skilled in the art (see for example, T. W. Greene, *Protecting Groups In Organic Synthesis*; Wiley: New York, Third Edition, 1999, and references cited therein.

The synthetic transformations described above are well known in the art and are generally described by reference works such as J. March, *Advanced Organic Chemistry, Reactions, Mechanisms and Structure*, (2nd Ed.), McGraw Hill: New York, 1977; Greg T. Hermanson in *Bioconjugate Techniques* (Academic Press, San Diego, Calif. (1996)); and F. Carey and R. Sundberg, *Advanced Organic Chemistry, Part B: Reactions and Synthesis*, $2^{nd}$ Ed., Plenum: New York, 1977; and references cited therein. Other useful synthetic techniques are described in U.S. Pat. No. 6,172,262 (McQuade et al.) and U.S. Patent Publication Nos. 2009/0270598 (Gellman et al.) and 2010/0311956 (Gellman et al.).

Amphiphile Applications to Proteins and Membranes

Manipulation of membrane proteins remains a profound technical challenge. A variety of different amphiphiles are needed on the market, as different amphiphiles are useful for different target proteins, depending on the properties of the protein and the in vitro use proposed. The best amphiphile for any particular protein is difficult or impossible to predict, and requires empirical testing. Researchers most often cannot predict which amphiphile will be suitably effective for manipulating a particular membrane protein. Data acquired for the new amphiphiles shows that they are comparable or superior to known detergents for membrane protein manipulation. Therefore the new amphiphiles described herein provide additional valuable tools for the manipulation of membrane proteins.

The invention provides compounds and compositions that can include a plurality of amphiphilic compounds described herein and a membrane protein, such as an integral membrane protein. Such compositions can take the form of aggregates or micelles, formed from a plurality amphiphilic compounds as described herein, optionally in conjunction with one or more other surfactant compounds and/or micelle-forming compounds, where the plurality of compounds surround the membrane protein. The composition can optionally include a polypeptide, a protein, and/or one or more other types of biological molecules complexed with the amphiphilic compound.

The invention thus provides methods of solubilizing a membrane protein by contacting the membrane protein with a plurality of a compound described herein, in an aqueous solution, thereby forming a solubilized aggregation of the compounds and the membrane protein. The invention also provides methods of stabilizing a membrane protein by contacting the membrane protein with a plurality of a compound described herein, in an aqueous solution, thereby forming an aggregation of the compounds and the membrane protein. The invention further provides methods of extracting a protein from a lipid bilayer by contacting the lipid bilayer with a plurality of a compound described herein in an aqueous solution to form a mixture, optionally in the presence of a buffer or other detergent, thereby forming an aggregation of the compounds and the membrane protein extracted from the lipid bilayer. The aggregation can then be separated from the mixture to provide isolated and/or purified membrane protein.

Accordingly, the invention provides various methods for manipulating membrane proteins. For example, a method is provided for solubilizing a membrane protein by contacting the protein in an aqueous environment with an effective amount of a compound as described herein, and optionally heating the protein and the compound, to provide the solubilized protein encapsulated in micelles of the compound. The effective amount of the compound can be an amount of the compound necessary to achieve its critical micelle concentration, to about 10 times, about 100 times, about 1,000 times, or about 10,000 times, the amount of the compound necessary to achieve its critical micelle concentration. The method can also include employing a buffer, heat, a second amphiphile or detergent, or other reagents, in the aqueous environment to aid in the solubilization and stabilization of membrane proteins.

The invention also provides a method of purifying a membrane protein by contacting the protein in an aqueous environment with an effective amount of a compound as described herein, to form micelles comprising a plurality of the compounds surrounding the protein, and isolating the micelles, to provide the purified membrane protein encapsulated in micelles of the compound. Other techniques for using the amphiphilic compounds described herein include techniques for stabilizing, crystallizing, and/or characterizing a protein while in a detergent micelle made up of a compound described herein.

The invention has several advantages over previous membrane manipulation technologies. For example, the amphiphiles described herein can lack any aromatic groups, therefore they are highly suitable for "optical" characterization methods such as UV absorbance spectroscopy and UV circular dichroism, when characterizing a protein solubilized by such amphiphiles.

Other uses of the amphiphiles described herein include their use as amphiphilic additions in crystallization trials, components of detergent mixtures, stabilizing factors in functional assays, detergents in exchange schemes, solubilization agents in cell-free expression reactions, as well as their use for separation on polyacrylamide gels using native protocols to maintain native states, for use in sample buffers on membrane fractions used to solubilize membrane proteins and to prepare proteins for separation on gels, and for use with Bug Buster® Protein Extraction Reagent formulations designed to break open cells and survey protein present, for example, without using sonication and/or lysozyme treatment and osmotic shock, such as with eukaryotic cell pellets that are relatively fragile and easily disrupted.

The amphiphiles described herein can also aid the formation of well-ordered crystals of membrane protein-amphiphile complexes. When a membrane protein-amphiphile complex crystallizes, amphiphiles can be included within the crystal lattice or in other embodiments, excluded from the crystal lattice. The amphiphiles can contribute to the ordering of proteins within the lattice when crystals are formed, thereby aiding the stability of growing membrane protein crystals.

The amphiphiles can stabilize membrane proteins, such as integral membrane proteins, in native conformations, for example, for protein structural characterization. The amphiphiles can extract proteins from lipid bilayers and stabilize the protein comparably or more effectively than conventional biological detergents. The amphiphiles can further be used for membrane protein research including isolation, stabilization, analysis by solution NMR, and biochemical and biophysical assay development.

The invention can therefore be directed to amphiphiles that can enhance the ability of a composition to solubilize and crystallize membrane-bound proteins into well-order crystals. The amphiphiles described herein can be used in any application where conventional detergents are used. For instance, the amphiphiles can be used to lyse cellular membranes. The amphiphiles can also form micelles in an aqueous solution. They can therefore be used to solubilize hydrophobic compounds for dispersion into aqueous solution. More specifically, the amphiphiles are useful for solubilizing membrane proteins, such as integral membrane proteins.

The amphiphiles described herein can be used alone, or in combination with other biological detergents, such as DDM, undecyl-β-D-maltoside (β-UDM), 3-[(3-cholamidopropyl)-dimethylammonio]-1-propanesulfonate (CHAPS), 3-[(3-cholamidopropyl)-dimethylammonio]-2-hydroxy-1-propanesulfonate (CHAPSO), lauryldimethylamine oxide (LDAO), octyl-glucoside (OG) or other detergents described by Hjelmeland in *Methods of Enzymology*, Vol. 124, page 135-164, which is incorporated herein by reference. For example, a particular detergent may to too harsh to suitable solubilize a membrane protein in its native conformation, however a combination of an amphiphiles described herein and a commercial biological detergents can provide reduced severity, thereby allowing the protein to be maintained in its native conformation while maintaining solubility.

Membrane Protein Manipulation

To assess the potential utility of new amphiphiles as tools for IMP manipulation, multiple protein systems were examined. DDM was used as a benchmark for conventional detergent performance in each case because DDM is very widely employed for IMP studies. Bacteriorhodopsin (bR) has been commonly used for evaluation of novel amphiphiles because stability can be assessed conveniently via spectrophotometry (Schafmeister et al., *Science* 1993, 262, 734-738; McQuade et al., *Angew. Chem.* 2000, 112, 774-777; *Angew. Chem. Int. Ed.* 2000, 39, 758-761).

bR was extracted from the native purple membrane with 2.0 wt % octyl-β-D-thioglucoside (OTG) (see Bazzacco at al., *Biomacromolecules* 2009, 10, 3317-3326). Following ultracentrifugation to remove insoluble debris, the bR solution was diluted with amphiphile solutions to give 0.2 wt %

Figure 2:
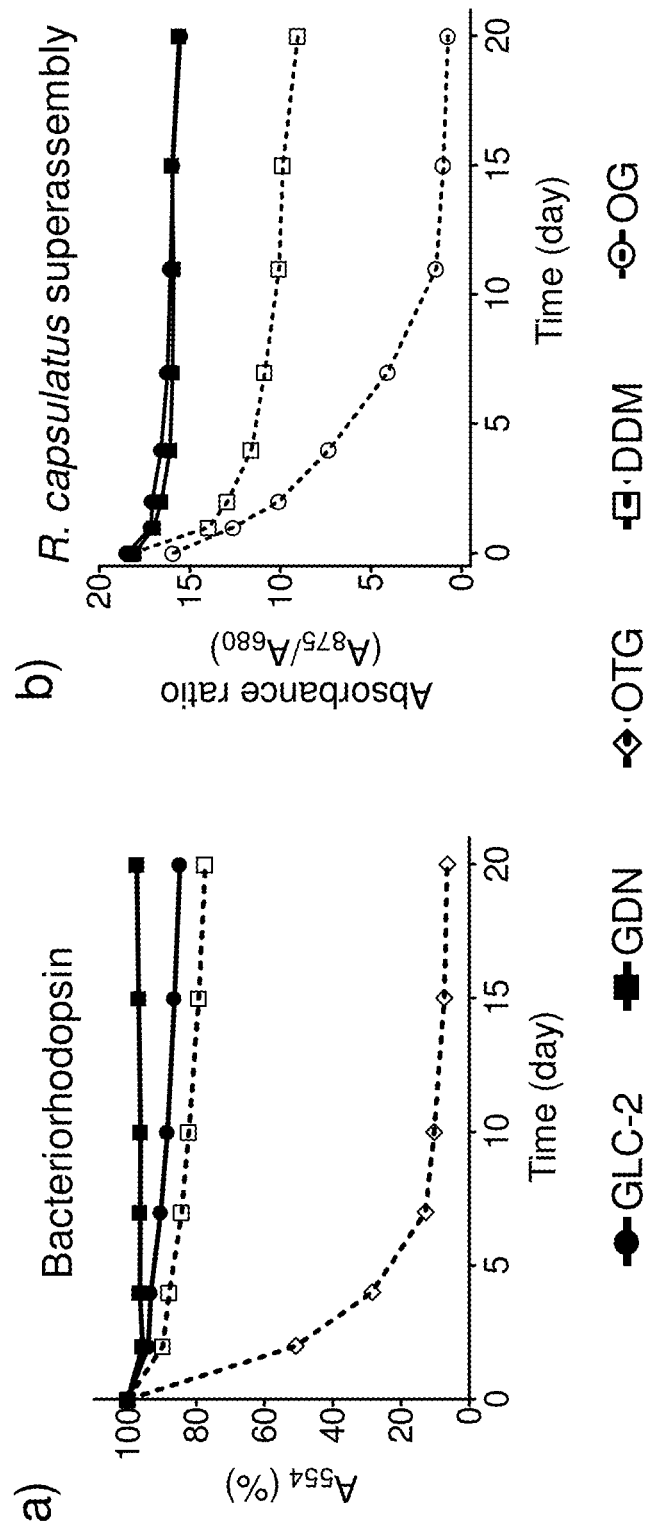
FIG. 2. Stability of (a) bR and (b) R. capsulatus LHI-RC superassembly at RT as a function of time. Agents were tested at 0.2 wt % OTG+1.6 wt % amphiphile for bR and at CMC+0.04 wt % for the R. capsulatus superassembly.
Figure 3:
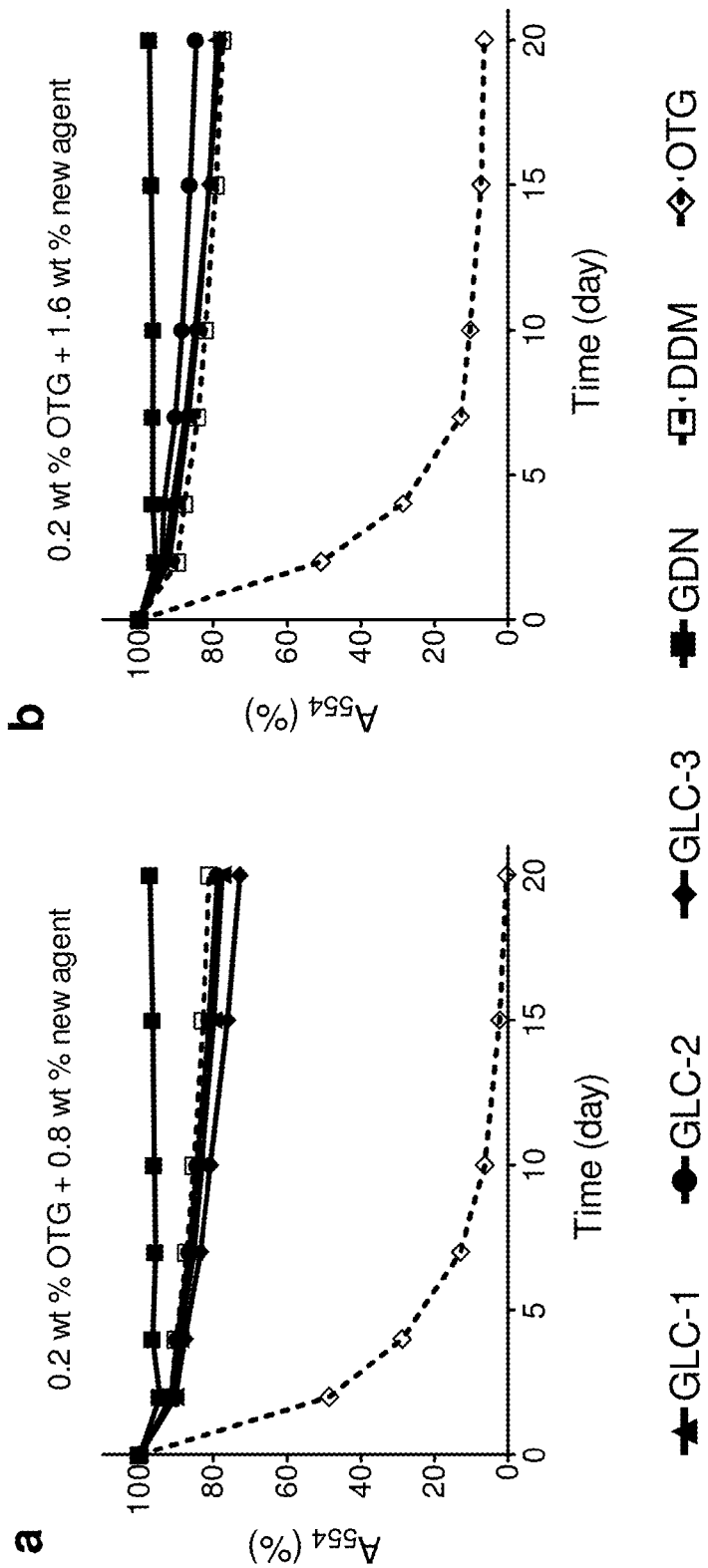
FIG. 3. Time course of bacteriorhodopsin (bR) stability at RT. OTG was mixed with each agent in a ratio of (a) 1:4 (0.2 wt % OTG+0.8 wt % GLCs/GDN) or (b) 1:8 (0.2 wt % OTG+1.6 wt % GLCs/GDN). Absorbance at 554 nm was followed for the long-term stability evaluation of the protein.

OTG+1.6 wt % new agent or DDM. The absorbance of the solutions at 554 nm was measured periodically over 20 days. FIG. 2a shows that two new agents, GLC-2 and GDN, are more effective than conventional detergents OTG and DDM at maintaining the native structure (see FIG. 3 for results with other agents). GDN provided exceptional stabilization properties, showing negligible loss in protein integrity after 20 days. When the assay was conducted at a lower amphiphile concentration, 0.2 wt % OTG+0.8 wt % new agent or DDM, similar results were obtained (FIG. 3).

Figure 4:
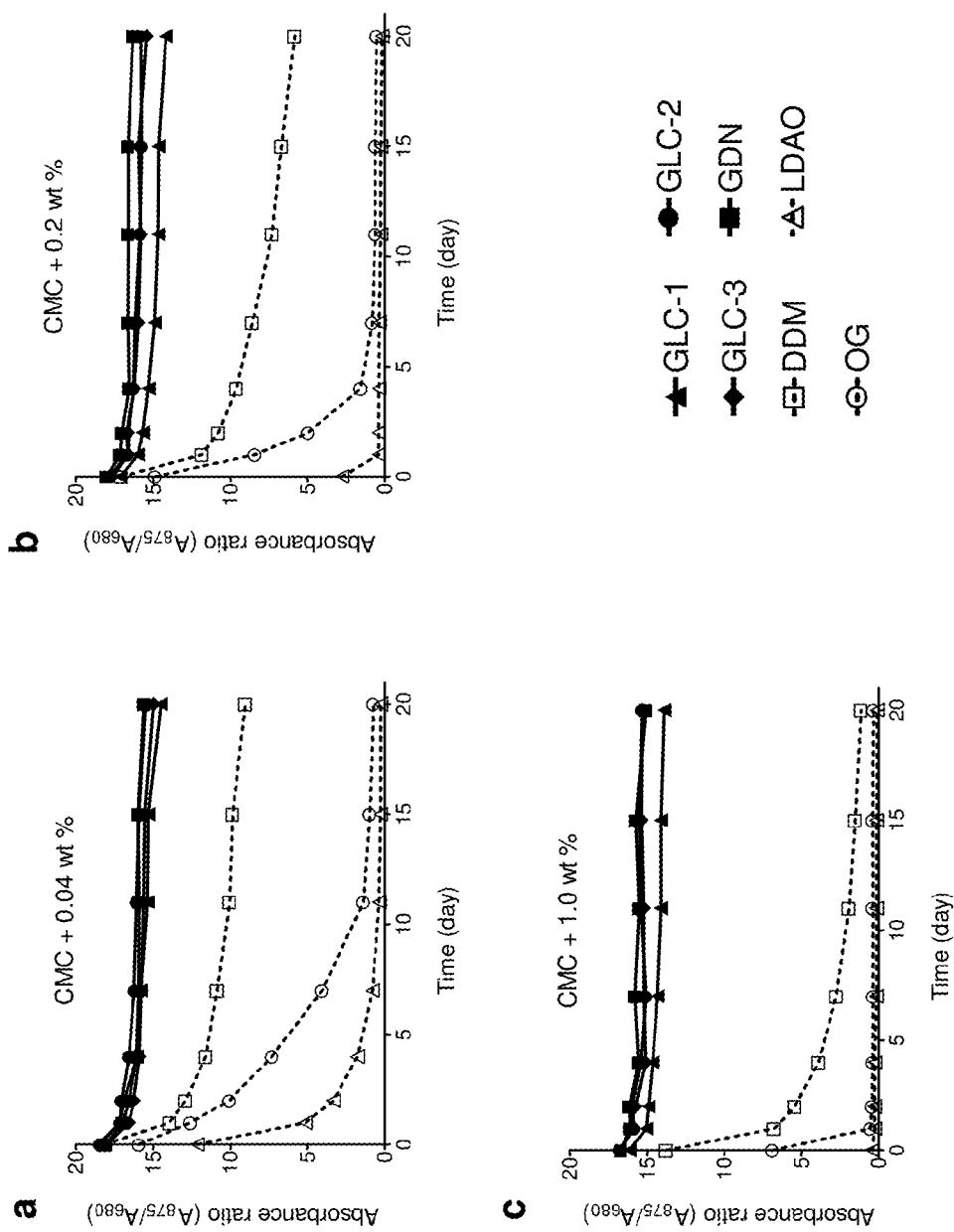
FIG. 4. Time course of LHI-RC complex stability at RT. The R. capsulatus superassembly was purified with each GLC or GDN at three different concentrations: (a) CMC+0.04 wt %, (b) CMC+0.20 wt % and (c) CMC+1.0 wt %. Absorbance ratio (A875/A680) was used as an indicator of superassembly integrity.

Next a more challenging system, the photosynthetic superassembly from *Rhodobacter capsulatus* (Laible et al., *Biochemistry* 2003, 42, 1718-1730), was analyzed. This photosynthetic superassembly contains the light harvesting I (LHI) complex and the reaction center (RC) complex. The superassembly contains >30 protein molecules; integrity can be assessed based on the 875 nm/680 nm absorbance ratio (Chae et al., *ChemBioChem* 2008, 9, 1706-1709). The superassembly was extracted from the native membrane with 1.0 wt % DDM and purified with DDM at its CMC (0.009 wt %). This preparation was diluted with solutions containing a new agent described herein, so that residual DDM (0.0004 wt %) was far below its CMC. The final concentration of each agent was CMC+0.04 wt %. FIG. 2b shows that the LHI-RC superassembly is substantially more stable over 20 days when solubilized by GLC-2 or GDN relative to solubilization with DDM or OG. Similar results were obtained with different detergent concentrations (FIG. 4).

Figure 5:
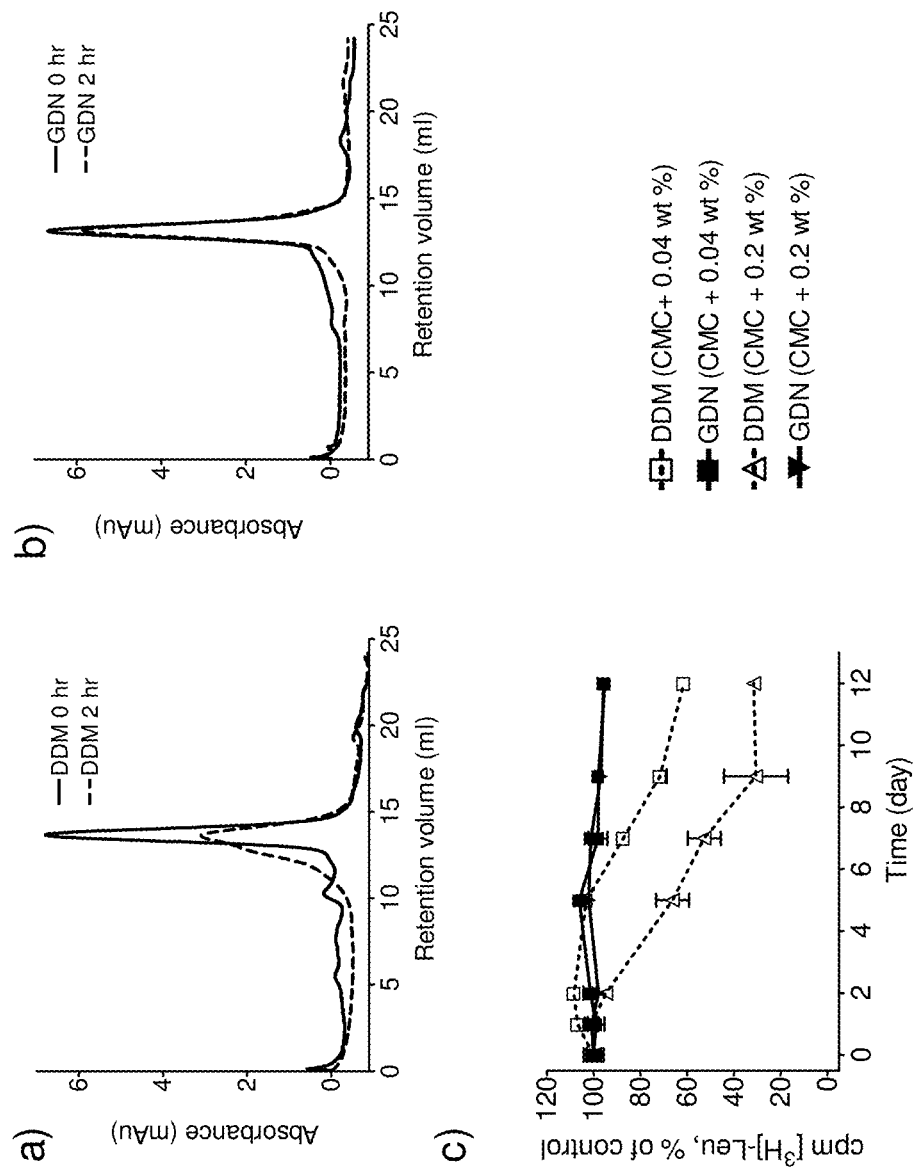
FIG. 5. (a, b) Gel filtration analysis for CMP-Sia and (c) activity over time of LeuT (scintillation proximity assay (SPA), based on [$^3$H]-Leu binding). Gel filtration analysis was performed at a detergent concentration of CMC+0.04 wt %, before or after incubation of solubilized CMP-Sia at 30° C. for 2 hr. SPA was conducted with detergents at CMC+0.04 wt % or CMC+0.2 wt % with LeuT stored at RT. SPA results are expressed as % activity relative to the day 0 measurements.

The promising behavior manifested by GDN in terms of the stability of bR and the *R. capsulatus* superassembly prompted the examining this amphiphile with another membrane protein, the murine cytidine-5'-monophosphate-sialic acid transporter (CMP-Sia) (Newstead et al., *Proc. Natl. Acad. Sci. USA* 2007, 104, 13936-13941). The protein was initially extracted from *S. cereviseae* membranes with 1% DDM and isolated in buffer containing 0.03% DDM. The final purified protein (6 mg/mL) was diluted 1:100 into solutions containing DDM or GDN at 0.042 wt % (which corresponds to CMC+0.033 wt % for DDM and CMC+0.04 wt % for GDN). The DDM- and GDN-solubilized CMP-Sia were analyzed by gel filtration before and after incubation for 2 hours at 30° C. (FIG. 5a, b).

Figure 6:
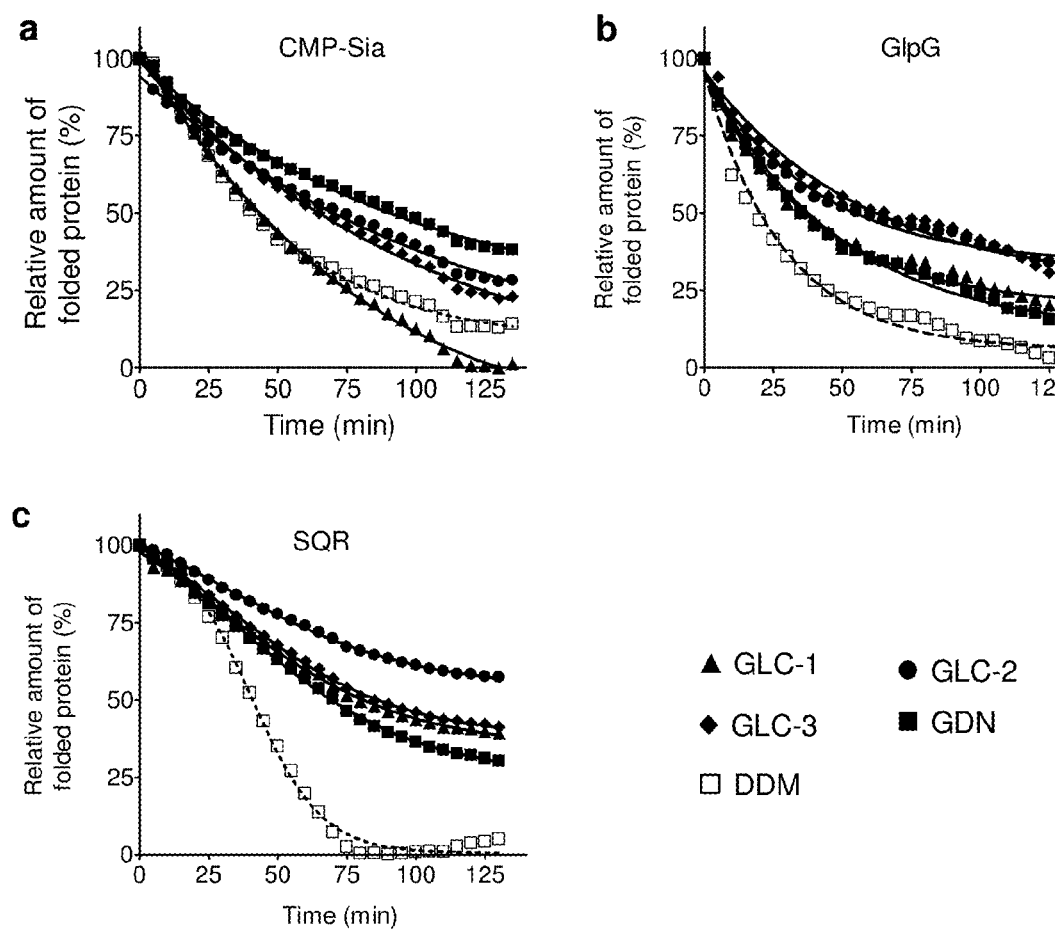
FIG. 6. CPM assays for (a) CMP-Sia, (b) GlpG and (c) SQR solubilized with each new amphiphile or DDM. The coumarin moiety of CPM is internally quenched by the maleimide unit, but the coumarin becomes fluorescent following reaction with Cys side chain thiol groups exposed upon protein unfolding. The CPM assay can therefore be used to monitor the extent of protein unfolding. CMP-Sia and GlpG were initially extracted from the native membrane with 1% DDM in PBS, 10 mM imidazole (pH 8.0), 150 mM NaCl, 10% glycerol, and isolated in 20 mM Tris (pH 7.5), 150 mM NaCl containing 0.03% DDM. SQR was extracted from the membrane using 2% $C_{12}E_9$ in 20 mM potassium phosphate (pH 7.4), 0.2 M EDTA, and isolated in 20 mM Tris (pH 7.6), 0.2% decyl-β-D-maltoside (DM). The purified proteins (CMP-Sia (6 mg/ml), GlpG (5 mg/ml) and SQR (12 mg/ml)) were diluted 1:150 in 20 mM Tris (pH 7.5), 150 mM NaCl containing CMC+0.04 wt % amphiphile or DDM. The CPM analysis was performed over 130 min at 30° C. using a microplate spectrofluorometer set at an excitation wavelength of 387 nm and an emission wavelength of 463 nm. Measurements were taken every 5 min after automatic agitation of the plate. The vertical axes in these graphs have no absolute meaning. The "Relative amount of folded protein" in each case is defined as follows: 100% corresponds to the fluorescence emission intensity at time=0 min; 0% corresponds to the lowest value measured among the amphiphile-treated samples for each protein during the 130 min assay period. Thus, for CMP-Sia, 0% is defined by the end-point measurement for protein solubilized with GLC-1. For GlpG and SQR, 0% is defined by the lowest value measured for protein solubilized with DDM. In no case can the "0%" value be interpreted as indicating that the protein is fully unfolded. This point is demonstrated by the gel filtration results shown for CMP-Sia in the description below (FIG. 5), which indicate that ~50% of the protein solubilized with DDM remains intact at the end of the incubation period; however, in FIG. 6a, DDM-solubilized CMP-Sia is indicated to contain ~20% "relative amount of folded protein" under the conditions used for the gel filtration analysis.

The results show GDN to be superior to DDM: CMP-Sia solubilized with DDM displays ~50% integrity after the 2 hour period, while GDN-solubilized protein retains >90% integrity. The favorable effect of GDN on CMP-Sia stability was further supported by N-[4-(7-diethylamino-4-methyl-3-coumarinyl) phenyl]maleimide (CPM) assay results when the membrane proteins were evaluated at CMC+0.04 wt % (FIG. 6a) (Alexandrov et al., Structure 2008, 16, 351-359). Two other membrane proteins were examined with the CPM assay, the rhomboid intramembrane serine protease GlpG (Urban, Biochem. J. 2010, 425, 501-521) and succinate:quinone oxidoreductase (SQR) (Horsefield et al., *Curr. Protein Pept. Sci.* 2004, 5, 107-118), both of which were expressed in *Escherichia coli*. In both cases, the results indicate that the new GLC/GDN amphiphiles are superior to DDM at maintaining native structure (FIGS. 6b and 6c).

Figure 7:
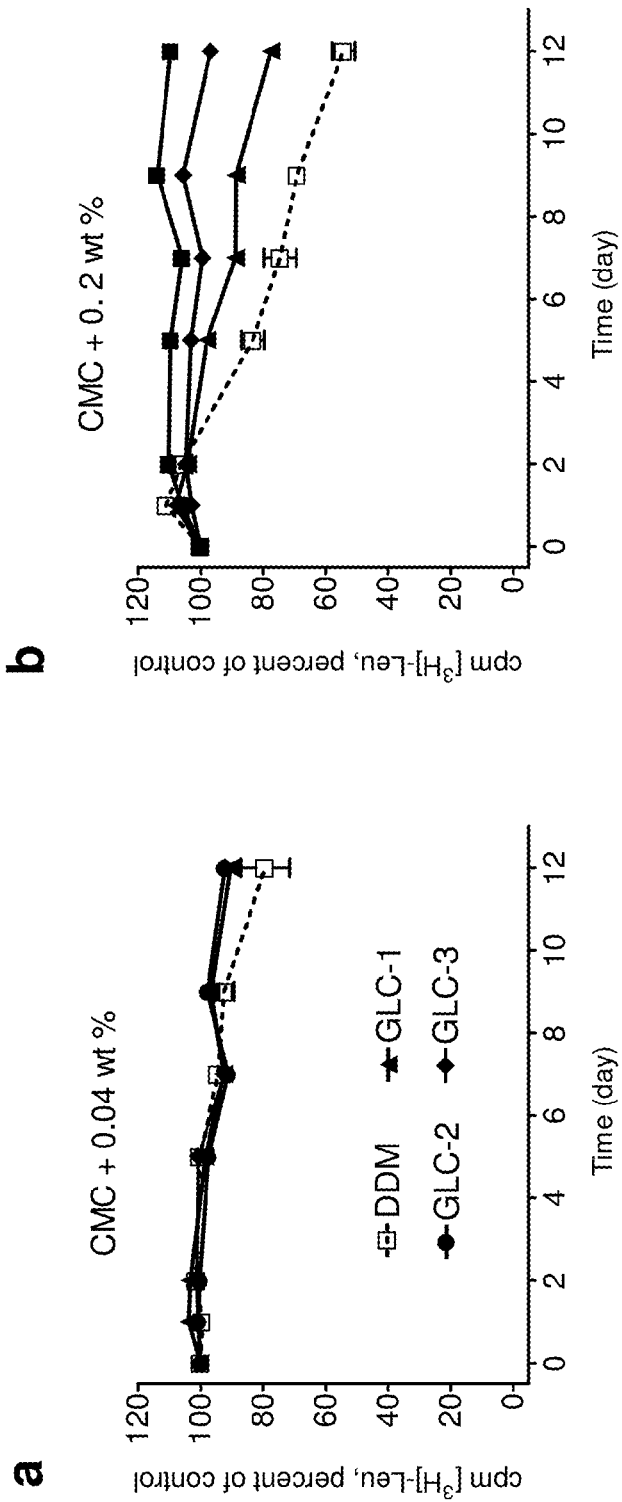
FIG. 7. Time course activity (scintillation proximity assay, SPA, based on [$^3$H]-Leu binding) for LeuT solubilized with GLC amphiphiles (GLC-1, GLC-2 or GLC-3) or DDM at (a) CMC+0.04 wt % and (b) CMC+0.20 wt %. SPA was conducted on protein stored at RT. Results are expressed as % of activity relative to the day 0 measurements (mean±s.e.m., n=2).

The new amphiphiles were then evaluated for the ability to maintain the leucine transporter (LeuT) from *Aquifex aeolicus* in a functional state (Quick and Javitch, *Proc. Natl. Acad. Sci. USA* 2007, 104, 3603-3608). The transporter was initially extracted with DDM and then diluted with amphiphile-containing solutions to generate amphiphile concentration of CMC+0.04 wt % or CMC+0.2 wt %. At both concentrations, GDN was very effective at maintaining LeuT activity, as indicated by binding of radiolabeled leucine, with preservation of >95% of initial activity after 12 days (FIG. 5c). In contrast, DDM-solubilized LeuT lost significant activity over this period. The GLC amphiphiles, too, were superior to DDM in terms of maintaining LeuT activity, although they did not match the effectiveness of GDN (FIG. 7).

Figure 8:
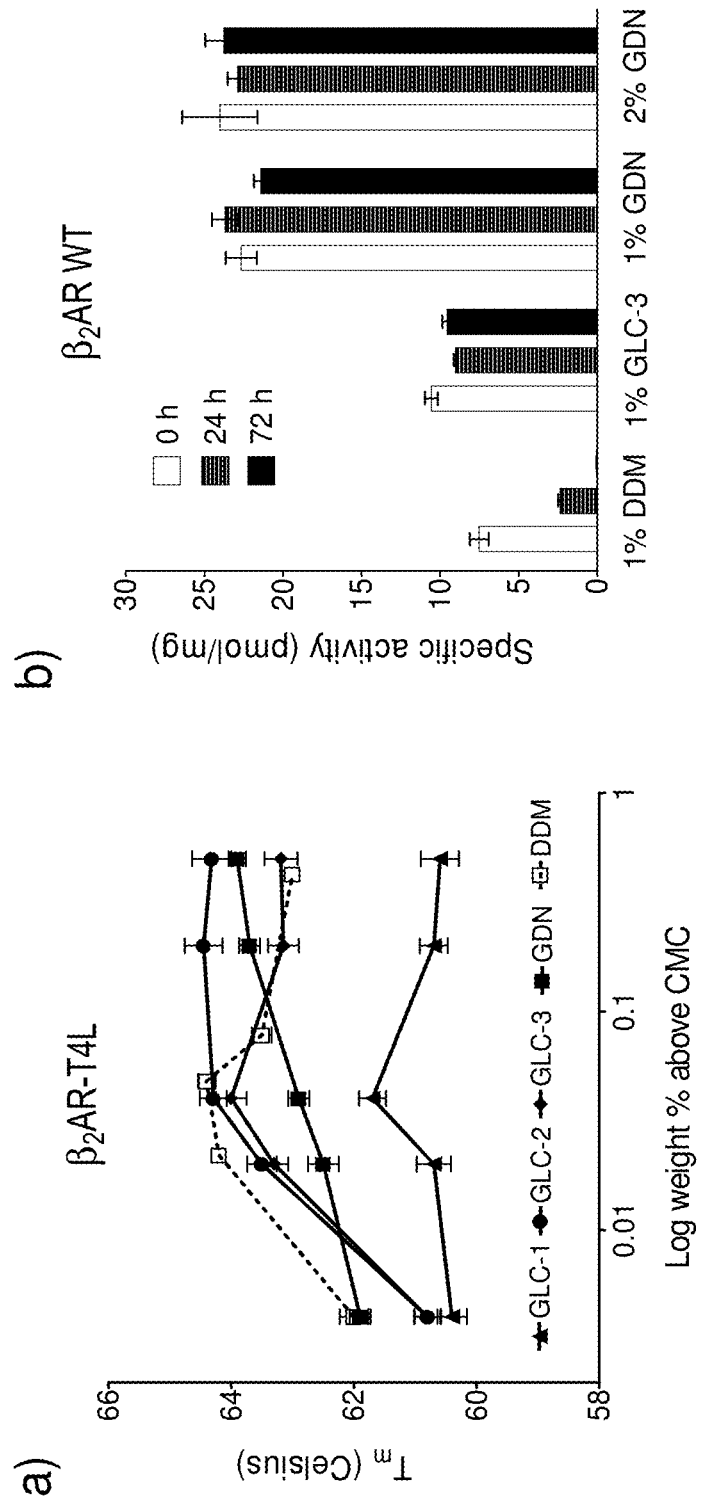
FIG. 8. a) Melting temperatures ($T_m$) of $\beta_2$AR-T4L, and b) $\beta_2$AR WT activity as a function of time, for proteins solubilized with new amphiphiles or DDM, demonstrating long-term stability properties of $\beta_2$AR stabilized by the new amphiphiles. $T_m$ values for $\beta_2$AR-T4L are plotted in terms of wt % of the amphiphile. $\beta_2$AR WT was extracted with 1 wt % or 2 wt % amphiphile, and activity was measured periodically by radioligand-binding assay using the antagonist [$^3$H]-dihydroalprenolol. The solubilized $\beta_2$AR WT samples were stored at 4° C.

To assess the new amphiphiles with a GPCR, a human 132 adrenergic receptor-T4-lysozyme fusion protein ($\beta_2$AR-T4L) was used (Rosenbaum et al., *Science* 2007, 318, 1266-1273). Stability was assessed via optical absorption measurements of $\beta_2$AR-T4L bound to the inverse agonist carazolol. $\beta_2$AR-T4L was initially solubilized and purified with DDM, and this detergent was then exchanged for the agent to be evaluated. The fluorescence emission maximum of carazolol occurs at 356 nm in aqueous solution, but emission is shifted to 341 nm in the receptor-bound state. The 341:356 nm peak intensity ratio was used to monitor the relative amounts of intact and denatured $\beta_2$AR-T4L, with $T_m$ defined as the temperature at which the 341:356 nm peak intensity ratio is half-way between that of fully native receptor and the fully denatured receptor. FIG. 8a shows how $T_m$ varies as a function of amphiphile concentration. At relatively low concentrations (<CMC+0.05 wt %), DDM was superior to the new amphiphiles. However, GLC-2 and GDN became superior to DDM at higher concentrations.

In the examples discussed above, conventional detergents such as DDM were used to extract IMPs from the membrane, and then in most cases the solution of detergent-solubilized protein was diluted with amphiphile-containing solutions to evaluate the new agents. With this approach it is possible that the small amount of residual conventional detergent could affect protein stability. To exclude this possibility, GLC-3 and GDN were used to extract wild type $\beta_2$AR ($\beta_2$AR WT) (Kobilka, *Trends in Pharmacological Sciences* 2011, 32, 213-218) from the membrane. Receptor activity was measured via a binding assay involving the antagonist [$^3$H]-dihydroalprenolol. The DDM-solubilized receptor showed low initial activity and rapidly decomposed (FIG. 8b). GLC-3-solubilized receptor showed initial activity similar to that of DDM, but in this case activity was maintained over 72 hours. GDN-solubilized $\beta_2$AR WT showed remarkable behavior: high initial activity (>3-fold increase relative to that seen with DDM) that did not vary over 72 hours. GDN is therefore highly suitable for GPCR extraction.

Figure 9:
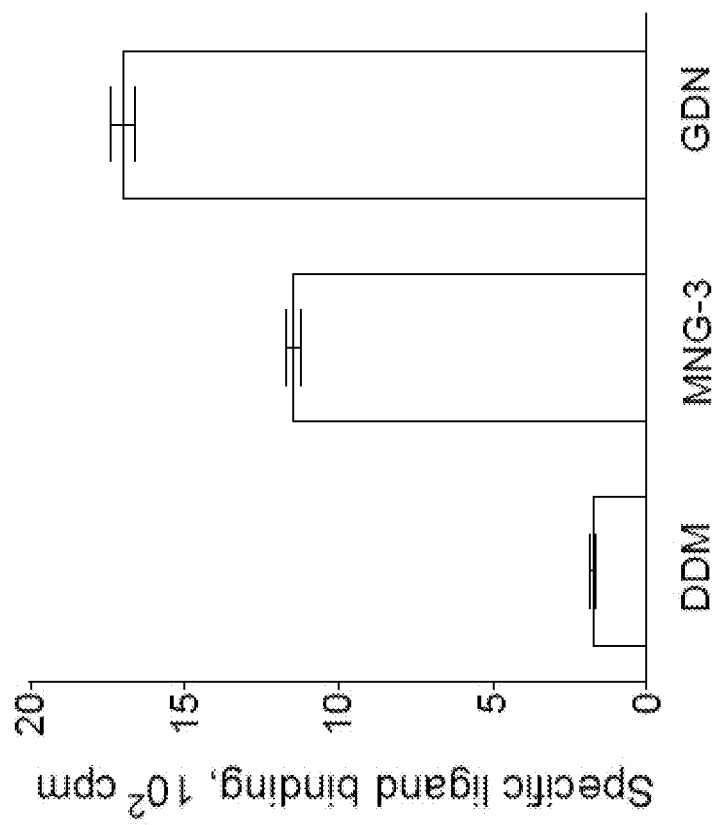
FIG. 9. Activity of δ-opioid receptor-T4L (δOR-T4L) solubilized with DDM, MNG-3 or GDN. The receptor was extracted with 1.0 wt % of amphiphile, and ligand binding activity (counts per minute (cpm)) was measured by radioligand-binding assay using the antagonist [$^3$H]-diprenorphine.

We turned to a δ-opioid receptor-T4L fusion (δOR-T4L), another GPCR, to compare GDN with the recently reported amphiphile MNG-3 (P. S. Chae, et al., *Nat. Methods* 2010, 7, 1003-1008), which has proven to be essential for crystallization of several other GPCR constructs (Rasmussen, et al., *Nature* 2011, 469, 236-240; Rosenbaum, et al., *Nature* 2011, 469, 175-180; Rasmussen, et al., *Nature* 2011, 477, 540-541; Kruse, et al., *Nature* 2012, 482, 552-556; Haga, et al., *Nature* 2012, 482, 547-551). Consistent with prior observations, MNG-3-solubilized δOR-T4L showed higher activity than DDM-solubilized δOR-T4L (FIG. 9). Remarkably, GDN-solubilized δOR-T4L displayed even higher activity. This data indicates that GDN is significantly effective for GPCR solubilization. The ability of the new amphiphiles to stabilize membrane proteins thus allows for the ability to perform analyses and structural studies that could not be performed with other detergents such as DDM because harsher detergents (e.g., DDM) can remove important lipid moieties from the proteins, causing them to denature and rapidly loose activity.

Figure 10:
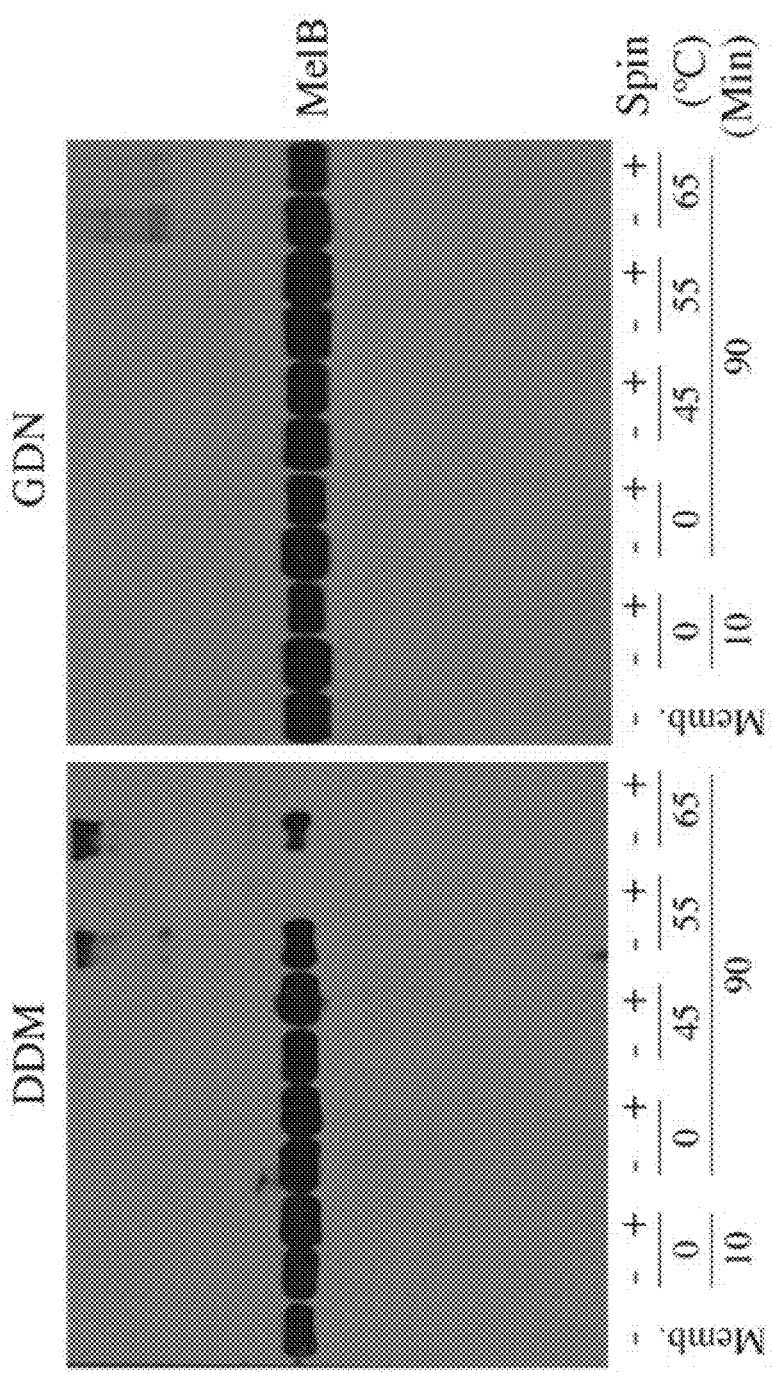
FIG. 10. SDS-12% PAGE and Western blot analysis of MelB. Samples were analyzed by SDS-PAGE analysis, and MelB was detected using anti-histidine tag antibody. Each sample contained 10 μg protein. For extracts generated with each detergent or amphiphile at each temperature, one sample was subjected to ultracentrifugation (+), and a comparison sample was not (−). As a control, an untreated membrane sample ("Memb."; no ultracentrifugation) was included in each gel.

Because GDN displayed particularly favorable behavior in the preceding studies, this agent was further characterized with melibiose permease (MelB), expressed in *Salmonella typhimurium* (Yousef and Guan, *Proc. Natl. Acad. Sci. USA* 2009, 106, 15291-15296). DDM (1.5 wt %) or GDN (1.5 wt %) was used to extract MelB from *S. typhimurium* membranes at 0° C. for 10 min or 90 min and then aggregated material was removed via ultracentrifugation. The amount of MelB in solution was determined by SDS-PAGE with immunoblot detection (FIG. 10). DDM could quantitatively extract MelB under these conditions; GDN was not quite as efficient in extraction, although a substantial yield of MelB was obtained.

Figure 11:
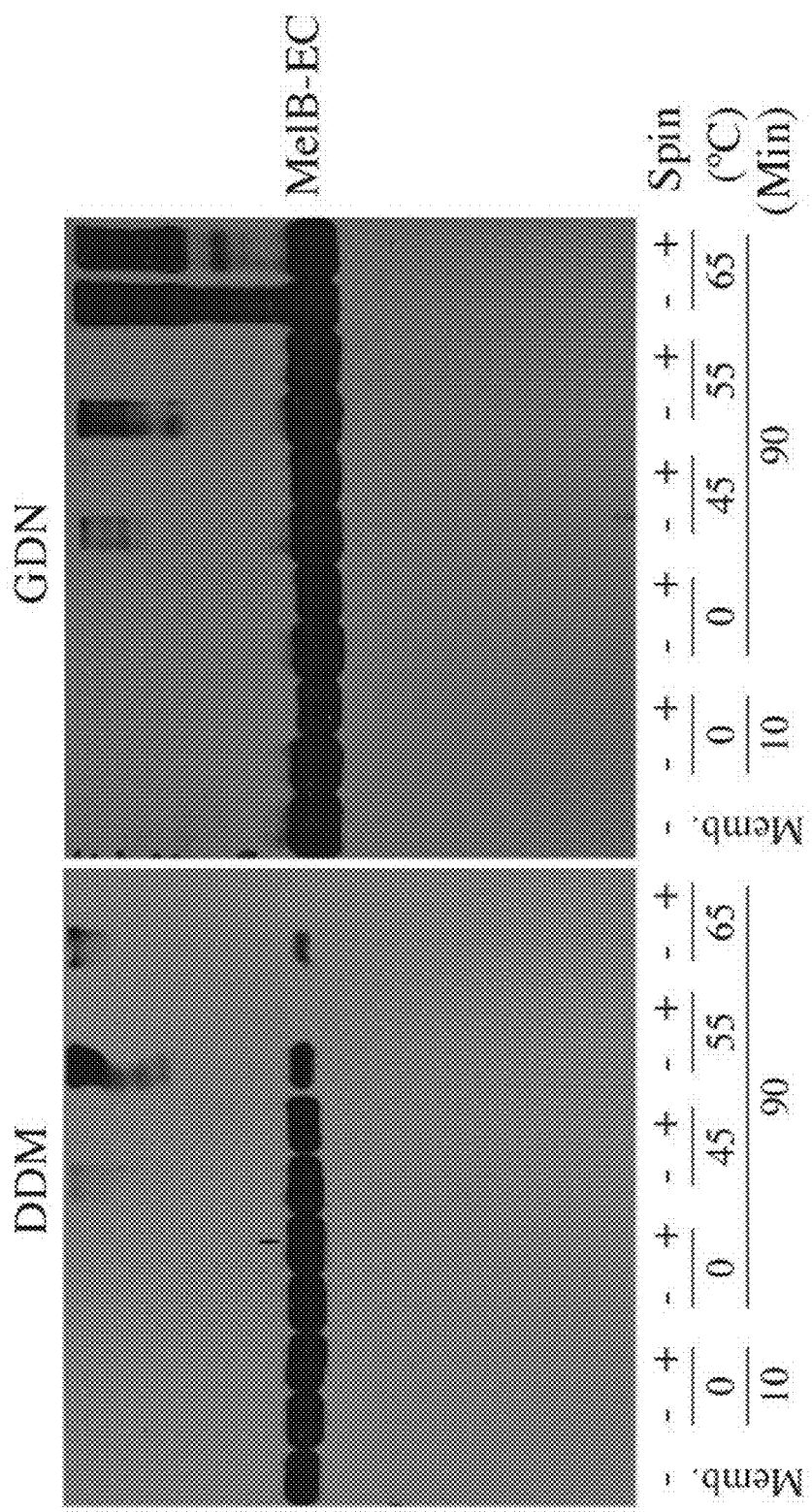
FIG. 11. SDS-12% PAGE and Western blot analysis of MelB-EC. MelB-EC protein was expressed in E. coli and treated with DDM or GDN for extraction. The samples were then separated by SDS-PAGE analysis, and detected by western blotting using anti-histidine tag antibody. Each sample included 10 μg proteins. For extracts with each detergent or amphiphile, one sample was subjected to ultracentrifugation (+) and a comparison sample was not (−). As a control, an untreated membrane sample ("Memb."; no ultracentrifugation) was included in each gel.

The effect of DDM and GDN on MelB thermostability was assessed by solubilizing the protein at the elevated temperatures for 90 min. DDM gave a high yield of soluble MelB at 45° C., but at 55° C. no soluble protein was obtained. Presumably MelB denatured and aggregated at the higher temperature in the presence of DDM. In contrast, GDN provided large amounts of soluble protein at 55° C. and even at 65° C. Interestingly, GDN could quantitatively extract the protein at elevated temperatures. This result indicates that GDN may be more useful for extracting membrane proteins at high temperatures relative to low temperatures (e.g., 4° C. or 25° C.). When MelB expressed in *E. coli* was used, similar results were obtained (FIG. 11).

Figure 12:
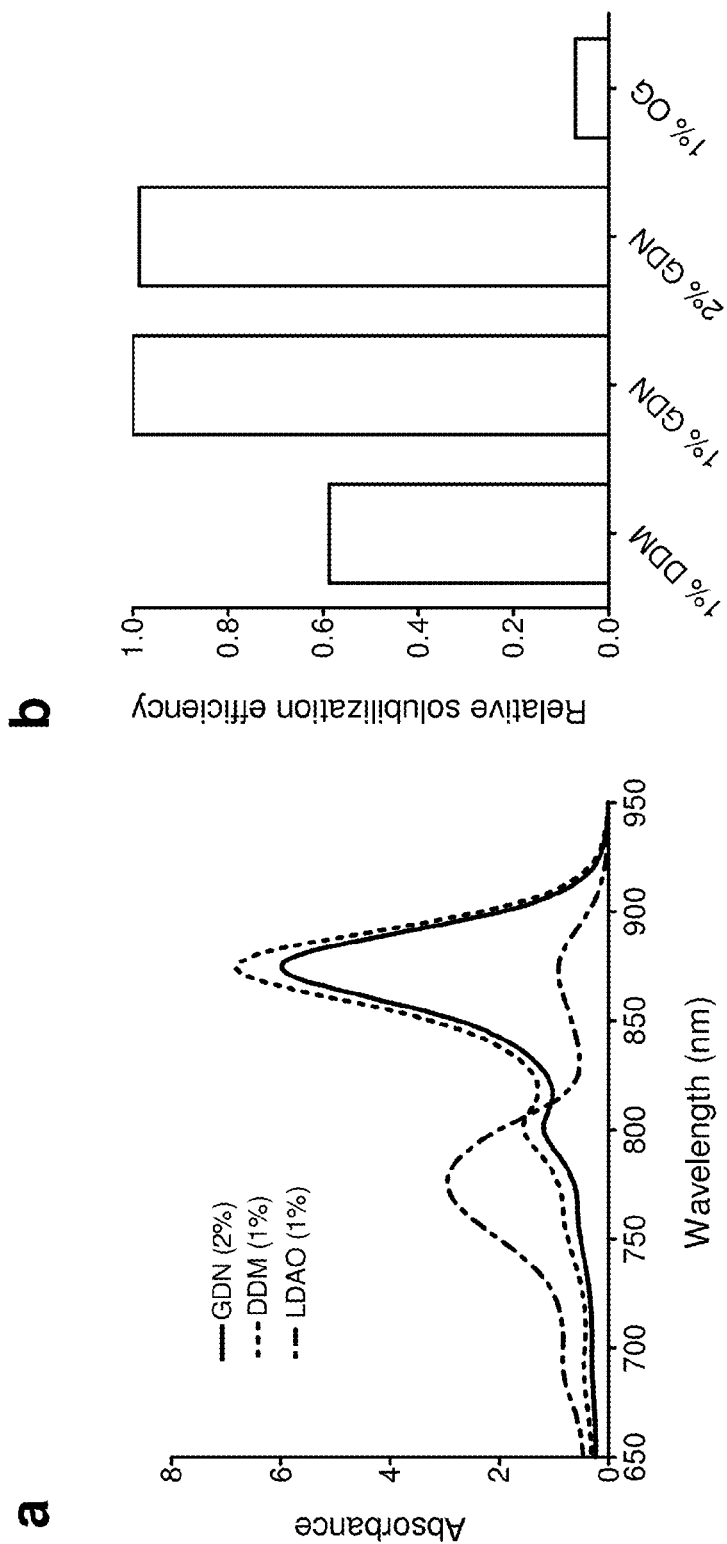
FIG. 12. The characterization of (a) LHI-RC complex and (b) $\beta_2$AR WT extracted with GDN or conventional detergents (DDM, laurydimethylamine-N-oxide (LDAO), and n-octyl-β-D-glucopyranoside (OG)). The superassembly amount was estimated via spectrophotometry and $\beta_2$AR WT was detected by western blotting using M1 antibody.

The favorable MelB extraction performance of GDN led to the examination of this amphiphile for extraction of other IMPs. Comparable results were obtained when the LHI-RC superassembly was extracted from *R. capsulatus* membranes with either 2 wt % GDN or 1 wt % DDM (GDN molecular weight is more than twice that of DDM) (FIG. 12a). For $\beta_2$AR WT extraction from insect cell membranes, 1 or 2 wt % GDN was more effective than was 1 wt % DDM; only a very small amount of $\beta_2$AR WT was detected with 1 wt % OG (FIG. 12b). DDM and GDN were used to extract a CMP-Sia fusion protein bearing green fluorescent protein (GFP) at the C-terminus, after expression in *Saccharomyces cerevisiae*; the amount of solubilized protein was estimated by total fluorescence. GDN (2 wt %), DDM (1 wt %) and OG (1 wt %) gave ~70%, ~80% and ~50% extraction yields, respectively. Overall, results with several systems show that GDN is generally very effective at extracting embedded proteins from biological membranes.

The results reported herein demonstrate that GDN is an extremely useful tool for membrane protein research. The GLC amphiphiles demonstrate useful behavior for several types of IMPs. It is particularly noteworthy that the tests described herein include membrane protein systems that vary in terms of structure and function. These studies have included systems, such as the *R. capsulatus* photosynthetic superassembly, LeuT, MelB and $\beta_2$AR, that display only limited stability when solubilized with conventional detergents. DDM is probably the most popular conventional detergent for IMP manipulations. The data described herein shows that GDN consistently matches or exceeds DDM in terms of both extracting and stabilizing diverse membrane proteins.

The MNG amphiphile series was recently reported (Chae et al., *Nat. Methods* 2010, 7, 1003-1008). The MNG molecules are structurally quite different from GDN and the MNG amphiphiles have already proven their worth by enabling the acquisition of new GPCR crystal structures (Rasmussen et al., *Nature* 2011, 469, 236-240; Rasmussen et al., *Nature* 2011, 469, 175-180; Rasmussen et al., *Nature* 2011, doi: 10.1038/nature10361). Although this disclosure does not directly compare the new steroidal agents with MNG amphiphiles, the fact that DDM was used as a benchmark for both studies allows for the conclusion that GDN is generally comparable to the best MNG examples identified to date for IMP extraction and solubilization, based on results with multiple IMP systems. Differences are evident in specific systems (e.g., GDN is a bit less effective than MNG amphiphiles in terms of $\beta_2$AR-T4L thermostability, but GDN is superior in terms of MelB thermostability). Because the MNG and GDN molecular structures are very different, these two types of amphiphile will manifest distinct and complementary advantages among the large set of membrane proteins that have yet to be tamed in the laboratory.

Typical detergents such as DDM, OG and LDAO have simple alkyl chains as the lipophilic groups. In the presence of a membrane protein, these amphiphiles associate with one another to cover the hydrophobic surfaces of the protein, resulting in protein-detergent complexes (PDCs). The overall architectures of the amphiphiles introduced herein are neither facially amphiphilic nor polymeric. Consequently, the new agents are anticipated to associate with membrane protein similarly to classical detergents. Since, however, the lipophilic groups of the new steroid-derived amphiphiles described herein are rigid and flat, these molecules will display a stronger tendency to associate with complementary protein surfaces than do conventional detergents, and this tendency underlies the favorable solubilization and stabilization properties documented herein.

Solubilization and Stability Assays

Light harvesting (LH) and reaction center (RC) complexes from photosynthetic bacteria (for example, *R. capsulatus*) are highly suitable for use in solubilization assays. These complexes, normally embedded in the bacterial membrane, are highly pigmented and several outcomes from an assay are possible, including no degradation, partial degradation or complete degradation upon solubilization, or no solubilization. Thus, graded comparative evaluations could be obtained for a set of candidates such as the carbohydrate-based amphiphiles described herein. In the engineered strain of *R. capsulatus* employed, the photosynthetic unit was comprised of a very labile LHI complex and a more resilient RC complex. An ideal amphiphile will extract the intact LHI-RC superassembly from a bacterial membrane preparation and maintain the natural interactions among the components. Amphiphiles with a more disruptive effect will dissociate and denature LHI, leaving only intact RC, and even harsher amphiphiles will cause RC degradation. Each of these various outcomes can be assessed unambiguously via optical spectroscopy.

Additional assays were carried out with reference to the following procedures. See also Example 3 below.

Bacteriorhodopsin Stability.

The procedure for the bR stability assay followed the protocol reported by Bazzacco and coworkers (*Biomacromolecules* 2009, 10, 3317-3326).

*R. capsulatus* Superassembly Stability.

The stability of *R. capsulatus* superassembly was assessed according to the protocol described by Chae and coworkers (*J. Am. Chem. Soc.* 2010, 132, 16750-16752).

Thermal Stability Assay for CMP-Sia, GlpG, and SQR.

The thermal stability assays of these membrane proteins were performed as described by Chae and coworkers (*J. Am. Chem. Soc.* 2010, 132, 16750-16752) using a temperature of 30° C. rather than 40° C.

CMP-Sia Gel Filtration.

Protein integrity was assessed using the procedure reported by Chae and coworkers (*Nat. Methods* 2010, 7, 1003-1008) using CMP-Sia instead of SQR.

LeuT Functional Assay.

LeuT functionality was measured according to the procedure reported by Chae and coworkers (*Nat. Methods* 2010, 7, 1003-1008).

$\beta_2$AR-T4L Stability.

Stability of $\beta_2$AR-T4L was assessed by measuring the melting temperature ($T_m$) of the receptor according to the procedure reported by Chae and coworkers (*Nat. Methods* 2010, 7, 1003-1008).

MelB Stability.

The protocol reported by Chae and coworkers (*Nat. Methods* 2010, 7, 1003-1008) was used to evaluate MelB stability with DDM and GDN.

Solubilization of *R. capsulatus* Superassembly, $\beta_2$AR WT and CMP-Sia Fusion Protein.

The procedure was performed according to the protocol reported by Chae and coworkers (*Nat. Methods* 2010, 7, 1003-1008).

The amphiphiles were thus evaluated as membrane protein solubilizers and stabilizers and they compared very favorably with DDM, a standard reagent in the field. Compared to DDM, for example, one of the evaluated amphiphiles forms micelles at one-tenth of the concentration required for DDM. Compared with DDM, GDN performs similarly for extracting membrane proteins from membranes, and stably retains the proteins in a soluble form within the micelles for substantially longer (>3 weeks) than DDM. Such improved stability (without sacrificing extraction efficiency) is a valuable trait for research tool amphiphiles.

The amphiphiles described herein require lower concentrations than many commonly used surfactants to form stable micelles. Also, proteins extracted with those amphiphiles demonstrate similar or higher activity and are extremely stable (i.e., remain soluble) in the micelle. In one example, the protein was stable in micelles of an amphiphile described herein for >3 weeks, whereas the DDM stabilized protein activity began to decay in a few hours or a few days.

The invention also provides a kit for enhancing the solubilization or stability of a proteinaceous macromolecule a biological sample, such as a membrane protein. The kit can include a solubilization reagent, such as an amphiphile described herein, to solubilize at least one protein in a biological sample, one or more reagents such as buffers, enzymes, solvents, and/or other surfactants, and optionally directions for the solubilization and/or recover a protein in a biological sample, and/or directions to isolate and/or resolve a protein in a biological sample.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Preparation of GLC Amphiphiles

A. Synthesis of Perbenzoylated Maltosylbromide.

This compound was prepared by following the reported protocol for perbenzoylated lactosylbromide (Kamath et al. *Carbohydr. Res.* 2004, 339, 1141-1146) with modifications as follows. To a solution of maltose monohydrate (30 g, 0.083 mol) in pyridine (300 mL) was added slowly benzoyl chloride (106 mL, 0.92 mol) and a catalytic amount (~0.2 g) of dimethylamino-pyridine (DMAP) at 0° C. The resulting solution was allowed to warm to RT and stirred for 20 hours at the same temperature. The solution was taken up with EtOAc (300 mL) and was washed with an iced aqueous 2N HCl solution until the aqueous phase became acidic. The neutralized organic layer was washed with brine (2×200 mL). The collected organic layer was dried over anhydrous $Na_2SO_4$ and removed by rotary evaporation to give crude syrup. This crude syrup was used for the next reaction without further purification. The crude material was dissolved in dried $CH_2Cl_2$ (100 mL) and to the solution was added 33 wt % HBr-acetic acid (100 mL) at 0° C. under $N_2$ conditions. The mixture was stirred at 0° C. for 4 hr. The solution was washed with iced water and saturated $NaHCO_3$ solution until the aqueous layer became slightly basic. The neutralized organic solution was washed with brine, dried over anhydrous $Na_2SO_4$ and removed by rotary evaporation to make crude syrup. The syrup was dissolved in ether (~500 mL) and stored at RT until white precipitates was formed. The white precipitates were collected on the glass filter and washed with ether three times. The filtered solid was dried in vacuo to afford perbenzoylated maltosylbromide as a white solid (80 g, 80% in two steps). This product was used for the next reaction without further purification. $^1$H NMR (300 MHz, $CDCl_3$): δ 8.13-8.06 (m, 2H), 8.02-7.96 (m, 2H), 7.91-7.84 (m, 4H), 7.77-7.64 (m, 4H), 7.69-7.63 (m, 2H), 7.63-7.15 (m, 21H), 6.76 (d, J=3.7 Hz, 2H), 6.16 (t, J=9.4 Hz, 2H), 6.10 (t, J=9.2 Hz, 1H), 5.79 (d, J=4.0 Hz, 1H), 5.68 (t, J=9.6 Hz, 1H), 5.28 (dd, J=10.8, 4.0 Hz, 1H), 5.09 (dd, J=10.0, 3.8 Hz, 1H), 4.96-4.87 (m, 1H), 4.84-4.75 (m, 1H), 4.72-4.62 (m, 3H), 4.59-4.39 (m, 1H).

B. General Procedure for Glycosylation Reactions.

This reaction was performed according to a literature method (Ashton et al., *Chem. Eur. J.* 1996, 2, 1115-1128) with slight modification. A mixture of hydroxyl-containing compound (having two hydroxyl groups), AgOTf (2.4 equiv.), and 2,4,6-collidine (1.8 equiv.) in anhydrous $CH_2Cl_2$ (40 mL) was stirred at −45° C. A solution of perbenzoylated maltosylbromide (2.4 equiv.) in $CH_2Cl_2$ (40 mL) was added dropwise over 0.5 hours to this suspension. Stirring was continued for 0.5 hours at −45° C., after which the reaction mixture was allowed to warm to 0° C. and was left stirring for 1.5 hours. After completion of reaction (as detected by TLC), pyridine was added and the reaction mixture was diluted with $CH_2Cl_2$ (40 mL) before being filtered over celite. The filtrate was washed successively with a 1 M aqueous $Na_2S_2O_3$ solution (40 mL), a 0.1 M aqueous HCl solution (40 mL), and brine (2×40 mL). The organic layer was then dried with anhydrous $Na_2SO_4$ and the solvents were removed by rotary evaporation. The residue was purified by silica gel column chromatography (EtOAc/hexane) providing desired product as a glassy solid.

C. General Procedure for De-O-Benzoylations Under Zemplén's Conditions.

The O-benzoylated compounds were dissolved in MeOH and then treated with the required amount of a methanolic solution of 0.5 M NaOMe such that the final concentration of NaOMe was 0.05 M. The reaction mixture was left stirring for 6 hours at room temperature, and then neutralized with Amberlite IR-120 (H$^+$ form) resin. The resin was removed by filtration and washed with MeOH and solvent was removed from the combined filtrate in vacuo. The residue was purified by silica gel column chromatography (MeOH/CH$_2$Cl$_2$). Further purification carried out by recrystallization using CH$_2$Cl$_2$/MeOH/diethyl ether afforded the fully de-O-benzoylated product as a white solid.

D. Synthesis and Characterization of GLC Amphiphiles.

Preparation of new amphiphiles GLC-1, GLC-2, and GLC-3 is illustrated in the synthetic schemes of FIGS. 13 and 14.

Compound 1 was synthesized by a modified literature protocol (Taotafa et al., *Org. Lett.* 2000, 2, 4117-4120). $^1$H NMR (300 MHz, CDCl$_3$): δ 3.26 (s, 3H), 3.24-3.08 (m, 1H), 2.46-2.32 (m, 1H), 2.32-2.16 (m, 1H), 1.96-1.50 (m, 10H), 1.50-0.94 (m, 18H), 0.94-0.82 (m, 6H), 0.64 (s, 3H); $^{13}$C NMR (75 MHz, CDCl$_3$): δ 80.7, 56.7, 56.2, 55.7, 43.0, 42.3, 40.6, 40.4, 36.1, 35.6, 35.5, 35.1, 32.9, 31.2, 31.0, 28.4, 27.6, 27.0, 26.6, 24.4, 23.6, 21.0, 18.5, 12.3; MS (MALDI-TOF): calcd. for C$_{25}$H$_{42}$O$_3$ [M+Na]$^+$ 413.3027. found 413.3017.

Compound 2. Methylated lithocholic acid (1) (1.5 g, 3.8 mmol), serinol (0.41 g, 4.6 mmol), 1-hydroxybenzotriazole monohydrate (HOBt) (0.61 g, 4.6 mmol) was dissolved in anhydrous DMF (30 mL). 1-β-(dimethylamino)propyl)-3-ethylcarbodiimide hydrochloride (EDC.HCl) (0.87 g, 4.55 mmol) was added in small portions at 0° C. and the resulting solution left stirring at room temperature for 20 h. The solution was taken up with EtOAc (100 mL) and was washed successively with a 1 M aqueous NaHCO$_3$ solution (100 mL), a 0.1 M aqueous HCl solution (100 mL) and brine (2×100 mL). Then the organic layer was dried with anhydrous Na$_2$SO$_4$ and the solvent was removed by rotary evaporation. The reaction mixture was precipitated with ether (100 mL) and the resulting solid was collected and dried in vacuo to afford amide-containing diol (2) as a white solid (1.60 g, 91%). This product was used for next reaction without further purification. $^1$H NMR (300 MHz, CDCl$_3$): δ 6.86 (d, J=7.9 Hz, 1H), 3.88-3.80 (m, 4H), 3.76-3.64 (m, 2H), 3.64-3.52 (m, 2H), 3.36 (s, 3H), 3.26-3.12 (m, 1H), 2.34-2.21 (m, 1H), 2.17-2.05 (m, 1H), 1.98-1.50 (m, 9H), 1.48-0.94 (m, 16H), 0.94-0.84 (m, 6H), 0.65 (s, 3H); $^{13}$C NMR (75 MHz, CDCl$_3$): δ 175.4, 80.7, 61.4, 56.5, 56.0, 55.4, 52.5, 49.3, 49.0, 48.7, 48.4, 42.8, 42.1, 40.4, 40.2, 35.9, 35.6, 35.2, 34.9, 32.7, 31.8, 28.2, 27.3, 26.7, 26.4, 24.2, 23.4, 20.8, 18.3, 12.0; MS (MALDI-TOF): calcd. for C$_{28}$H$_{49}$NO$_4$ [M+Na]$^+$ 486.3554. found 486.3570.

Compound 3. LiAlH$_4$ (0.44 g, 1.5 mmol) was added slowly to compound 1 (1.5 g, 3.8 mmol) dissolved in THF (50 mL) at 0° C. The mixture was stirred at RT for 1 day, quenched with MeOH, water, a 1 N aqueous HCl solution successively at 0° C. and then extracted with diethyl ether (2×50 mL). The combined organic layer was washed with brine and dried with anhydrous Na$_2$SO$_4$. The residue was purified by silica gel column chromatography (EtOAc/hexane) providing a desired product (3) as a white solid (1.3 g, 89%). $^1$H NMR (300 MHz, CDCl$_3$): δ 3.60 (t, J=6.0 Hz, 2H), 3.34 (s, 3H), 3.21-3.11 (m, 1H), 2.01-1.51 (m, 10H), 1.50-0.96 (m, 18H), 0.96-0.82 (m, 6H), 0.64 (m, 3H); $^{13}$C NMR (75 MHz, CDCl$_3$): δ 80.6, 63.7, 56.7, 56.4, 55.7, 42.9, 42.2, 40.5, 40.4, 36.0 35.8, 35.5, 35.1, 32.9, 32.0, 29.6, 28.5, 27.5, 27.0, 26.6, 24.4, 23.6, 21.0, 18.8, 12.2; MS (MALDI-TOF): calcd. for C$_{25}$H$_{44}$O$_2$ [M+NH$_4$]$^+$ 394.3680. found 394.3683.

Compound 4. To a solution of alcohol (3) (0.88 g, 2.3 mmol) and carbon tetrabromide (0.79 g, 3.0 mmol) in CH$_2$Cl$_2$ (100 mL) was added triphenylphosphine (Ph$_3$P) at 0° C. The solution was stirred at 0° C. for 1 hr and then continued the stirring at RT for 15 hr. The solvent was evaporated and then the 1:15 mixture of CH$_2$Cl$_2$ and hexane (100 mL) was added to the residue to precipitate out the oxidized side product of triphenylphosphine. After filtration and evaporation, the residue was purified by silica gel column chromatography (EtOAc/hexane) providing a desired product (4) as a white solid (0.92 g, 90%). $^1$H NMR (300 MHz, CD$_3$OD): δ 3.43-3.29 (m, 5H), 3.21-3.09 (m, 1H), 2.01-1.47 (m, 11H), 1.47-0.99 (m, 17H), 0.99-0.84 (m, 7H), 0.64 (s, 3H); $^{13}$C NMR (75 MHz, CD$_3$OD): δ 80.6, 56.8, 56.7, 56.3, 55.8, 42.9, 42.3, 40.4, 36.1, 35.5, 35.4, 35.1, 34.8, 34.7, 33.0, 29.9, 28.5, 27.6, 27.0, 26.6, 24.4, 23.6, 21.0, 18.9, 12.3; MS (MALDI-TOF): calcd. for C$_{25}$H$_{43}$O$_2$Br [M+NH$_4$]$^+$ 456.2836. found 456.2118.

Compound 5. 1,1,1-Tris(hydroxymethyl)ethane (1.3 g, 11.2 mmol) is dissolved in 40 mL of DMF and NaH (0.45 g, 11.2 mmol) was added. Bromide (4) (1.6 g, 3.7 mmol) was added to this solution and the mixture was stirred for 2 hr at 60° C. After adding water (100 mL), the resulting residue was extracted with ether (2×100 mL). The combined organic layer was washed with brine and dried with anhydrous Na$_2$SO$_4$. The residue was purified by silica gel column chromatography (EtOAc/hexane) providing alkyl-containing diol (5) as a white solid (1.1 g, 60%). $^1$H NMR (300 MHz, CD$_3$OD): δ 3.69 (d, J=11.0 Hz, 2H), 3.56 (d, J=11.0 Hz, 2H), 3.46-3.34 (m, 7H), 3.21-3.11 (m, 1H), 3.01-2.79 (br s, 2H), 2.01-1.57 (m, 9H), 1.57-0.92 (m, 20H), 0.92-0.71 (m, 11H), 0.63 (s, 3H); $^{13}$C NMR (75 MHz, CD$_3$OD): δ 80.6, 77.0, 72.5, 67.9, 56.6, 56.2, 56.2, 55.6, 42.9, 42.8, 42.2, 40.9, 40.8, 40.5, 40.3, 36.0, 35.7, 35.4, 35.1, 35.0, 32.3, 28.4, 27.4, 26.9, 26.5, 26.2, 24.3, 23.5, 20.9, 18.8, 18.6, 17.3, 12.2; MS (MALDI-TOF): calcd. for C$_{30}$H$_{54}$O$_4$ [M+H]$^+$ 479.4095. found 479.4096.

Compound 6. To a solution of bromide (4; 0.92 g, 2.1 mmol) and diethyl malonate (1.6 g, 10.4 mmol) in 1:1 mixture of THF and DMF (80 mL) was added K$_2$CO$_3$ (1.5 g, 10.5 mmol). The mixture was heated at 90° C. for 15 hr, quenched with water (100 mL) at 0° C. and then extracted with diethyl ether (2×100 mL). The combined organic layer was washed with brine and dried with anhydrous Na$_2$SO$_4$. The crude product was used for the next reaction without further purification. The crude product was dissolved in THF (50 mL) and LiAlH$_4$ (0.52 g, 14.0 mmol) was added slowly to the solution at 0° C. The mixture was stirred at RT for 1 day, quenched with MeOH, water, a 1 N aqueous HCl solution successively at 0° C. and then extracted with diethyl ether (2×50 mL). The combined organic layer was washed with brine and dried with anhydrous Na$_2$SO$_4$. The residue was purified by silica gel column chromatography (EtOAc/hexane) providing alkyl-containing diol (6) as a white solid (0.85 g, 93% (two steps)). $^1$H NMR (300 MHz, CD$_3$OD): 3.89-3.81 (m, 2H), 3.67-3.59 (m, 2H), 3.35 (s, 3H), 3.24-3.10 (m, 1H), 3.54 (br s, 2H), 2.02-1.48 (m, 10H), 1.48-0.92 (m, 25H), 0.92-0.71 (m, 10H), 0.63 (s, 3H); $^{13}$C NMR (75 MHz, CD$_3$OD): δ 80.7, 67.1, 66.8, 56.7, 56.5, 55.7, 42.9, 42.3, 40.6, 40.4, 36.4, 36.1, 35.9, 35.5, 35.1, 33.0, 28.6, 28.4, 27.5, 27.0, 26.6, 24.4, 24.0, 23.6, 21.0, 18.8, 12.2; MS (MALDI-TOF): calcd. for C$_{28}$H$_{50}$O$_3$ [M+NH$_4$]$^+$ 452.4099. found 452.4102.

GLC-1a was synthesized according to the general procedure for glycosylation. $^1$H NMR (300 MHz, CD$_3$OD): 5.77 (d, J=8.1 Hz, 1H), 5.44-5.19 (m, 5H), 5.06 (dt, J=10.2, 2.0 Hz, 2H), 4.90-4.75 (m, 4H), 4.55-4.43 (m, 4H), 4.32-4.15 (m, 5H), 4.09-3.93 (m, 6H), 3.80-3.67 (m, 4H), 3.56-3.46 (m, 1H), 3.35 (m, 3H), 3.23-3.09 (m, 1 h), 2.16 (s, 6H), 2.11 (s, 6H), 2.08-1.93 (m, 32H), 1.93-0.95 (m, 29H), 0.95-0.80 (m, 8H), 0.63 (s, 3H); $^{13}$C NMR (75 MHz, CD$_3$OD): δ 173.5, 170.7, 170.6, 170.5, 170.3, 170.2, 170.1, 169.9, 169.8, 169.6, 101.0, 100.8, 95.8, 80.6, 75.4, 75.2, 73.0, 72.9, 72.6, 72.5, 72.4, 72.2, 70.2, 69.5, 68.7, 68.6, 68.2, 62.9, 61.6, 56.2, 55.7, 42.9, 42.2, 40.5, 40.4, 36.0, 35.7, 35.0, 33.5, 33.0, 31.7, 28.4, 27.5, 27.0, 24.4, 23.6, 21.1, 21.0, 20.9, 20.8, 18.6, 12.2; MS (MALDI-TOF): calcd. for C$_{150}$H$_{145}$NO$_{38}$ [M+Na]$^+$ 2590.9. found 2591.4.

GLC-2a was synthesized according to the general procedure for glycosylation. $^1$H NMR (300 MHz, CD$_3$OD): 8.12-8.02 (m, 4H), 8.02-7.95 (m, 7H), 7.95-7.88 (m, 4H), 7.88-7.83 (m, 4H), 7.83-7.77 (m, 4H), 7.77-7.67 (m, 4H), 7.67-7.16 (m, 45H), 6.13 (t, J=10.0 Hz, 2H), 5.72-5.60 (m, 4H), 5.39 (t, J=9.5 Hz, 2H), 5.20-5.08 (m, 4H), 4.70-4.43 (m, 4H), 4.40-4.16 (m, 8H), 3.56-3.37 (m, 5H), 3.34 (s, 3H), 3.26-3.12 (m, 2H), 3.06 (q, J=10.1 Hz, 2H), 2.98-2.89 (m, 3H), 2.84 (d, J=9.2 Hz, 1H), 1.95-0.95 (m, 34H), 0.95-0.82 (m, 6H), 0.82-0.73 (m, 6H), 0.59 (s, 3H); $^{13}$C NMR (75 MHz, CD$_3$OD): δ 166.3, 166.2, 166.0, 165.7, 165.2, 165.0, 133.9, 133.7, 133.6, 133.4, 133.3, 133.2, 130.1, 129.9, 129.8, 129.6, 129.3, 129.2, 129.1, 129.0, 128.9, 128.8, 128.6, 128.5, 128.4, 128.3, 101.1, 101.0, 95.9, 80.6, 74.8, 73.6, 72.5, 72.4, 72.3, 71.4, 70.0, 69.2, 69.1, 66.0, 63.5, 62.7, 56.6, 56.3, 55.7, 42.8, 42.2, 40.5, 40.4, 40.3, 36.0, 35.6, 35.5, 35.1, 33.0, 32.2, 28.4, 27.5, 27.0, 26.6, 26.2, 24.4, 23.6, 21.0, 18.8, 17.2, 15.4, 14.4, 12.2; MS (MALDI-TOF): calcd. for C$_{152}$H$_{150}$O$_{38}$ [M+Na]$^+$ 2606.0. found 2606.5.

GLC-3a was synthesized according to the general procedure for glycosylation. $^1$H NMR (300 MHz, CD$_3$OD): 8.10-7.90 (m, 15H), 7.89-7.83 (m, 4H), 7.83-7.76 (m, 4H), 7.76-7.68 (m, 4H), 7.68-7.13 (m, 42H), 6.13 (t, J=10.0 Hz, 2H), 5.74-5.59 (m, 4H), 5.41-5.30 (m, 2H), 5.21-5.06 (m, 4H), 4.72-4.48 (m, 4H), 4.41-4.16 (m, 8H), 3.69-3.56 (m, 2H), 3.34 (s, 3H), 3.34-3.25 (m, 2H), 3.21-3.10 (m, 1H), 3.10-2.92 (m, 2H), 2.79 (t, J=9.8 Hz, 1H), 1.92-1.44 (m, 11H), 1.44-1.09 (m, 15H), 1.09-0.79 (m, 14H), 0.79-0.69 (m, 3H), 0.56 (s, 3H) $^{13}$C NMR (75 MHz, CD$_3$OD): δ 166.3, 166.0, 165.7, 165.2, 165.1, 165.0, 133.7, 133.6, 133.4, 133.3, 130.2, 130.1, 130.0, 129.8, 129.7, 129.6, 129.5, 129.4, 129.2, 129.1, 129.0, 128.6, 128.4, 101.2, 95.8, 80.6, 77.4, 74.8, 74.7, 72.2, 71.4, 70.0, 69.1, 62.7, 60.6, 56.6, 55.7, 42.8, 42.3, 40.5, 40.3, 36.0, 35.9, 35.5, 35.1, 33.0, 28.5, 28.2, 27.5, 27.0, 24.4, 23.9, 23.6, 21.2, 21.0, 18.7, 14.4, 12.2; MS (MALDI-TOF): calcd. for C$_{150}$H$_{146}$O$_{37}$ [M+Na]$^+$ 2561.9. found 2562.5.

GLC-1 was synthesized according to the general procedure for de-O-benzoylation. $^1$H NMR (300 MHz, CDCl$_3$): δ 5.15 (d, J=3.6 Hz, 2H), 4.33 (t, J=7.0 Hz, 2H), 4.01-3.74 (m, 9H), 3.73-3.15 (m, 25H), 2.36-2.20 (m, 1H), 2.20-2.06 (m, 1H), 2.06-1.52 (m, 10H), 1.52-1.02 (m, 18H), 1.02-0.88 (m, 7H), 0.69 (s, 3H); $^{13}$C NMR (75 MHz, CDCl$_3$): δ 176.9, 103.0, 82.1, 81.4, 77.8, 76.7, 75.2, 74.9, 74.8, 74.7, 74.2, 71.6, 62.8, 58.0, 57.5, 56.0, 44.0, 43.5, 42.0, 37.3, 37.0, 36.1, 28.5, 27.8, 24.1, 22.1, 19.1, 12.8; MS (MALDI-TOF): calcd. for C$_{52}$H$_{89}$O$_{24}$ [M+Na]$^+$ 1134.5667. found 1134.5703.

GLC-2 was synthesized according to the general procedure for de-O-benzoylation. $^1$H NMR (300 MHz, CDCl$_3$): δ 5.19 (d, J=3.6 Hz, 2H), 4.35 (t, J=7.7 Hz, 2H), 4.00-3.77 (m, 8H), 3.77-3.51 (m, 12H), 3.51-3.14 (m, 15H), 2.11-1.05 (m, 26H), 1.05-0.91 (m, 9H), 0.72 (s, 3H); $^{13}$C NMR (75 MHz, CDCl$_3$): δ 105.1, 103.0, 82.2, 81.5, 78.0, 76.7, 75.2, 74.9, 74.3, 73.6, 73.4, 73.2, 71.6, 62.9, 62.3, 58.0, 57.8, 56.0, 44.0, 43.5, 42.1, 42.0, 41.7, 37.4, 37.0, 36.4, 36.1, 34.0, 33.7, 29.6, 28.5, 27.9, 27.8, 27.5, 25.4, 24.1, 22.1, 19.4, 18.0, 12.7; MS (MALDI-TOF): calcd. for C$_{54}$H$_{94}$O$_{24}$ [M+Na]$^+$ 1149.6027. found 1149.6029.

GLC-3 was synthesized according to the general procedure for de-O-benzoylation. $^1$H NMR (300 MHz, CDCl$_3$): δ 5.16 (d, J=3.6 Hz, 2H), 4.32 (t, J=7.7 Hz, 2H), 3.99-3.74 (m, 8H), 3.74-3.55 (m, 10H), 3.55-3.15 (m, 12H), 2.10-1.02 (m, 31H), 1.02-0.83 (m, 7H), 0.68 (s, 3H); $^{13}$C NMR (75 MHz, CDCl$_3$): δ 104.9, 104.8, 103.0, 82.2, 81.5, 78.0, 76.7, 75.2, 74.9, 74.3, 71.6, 71.4, 62.9, 62.4, 58.0, 57.9, 56.0, 44.0, 43.6, 42.0, 41.7, 40.9, 37.6, 37.4, 37.2, 36.4, 36.1, 34.0, 30.0, 29.6, 28.5, 28.0, 27.8, 25.4, 24.8, 24.1, 22.1, 19.4, 12.7; MS (MALDI-TOF): calcd. for C$_{52}$H$_{90}$O$_{23}$ [M+Na]$^+$ 1105.5766. found 1105.5719.

Example 2

Preparation of GDN Amphiphiles

The synthetic scheme for the preparation of amphiphile GDN is illustrated in FIG. 15.

Compound 7. Ethyl diazoacetate (1.8 g, 15.7 mmol) was added to a solution of diosgenin (5.0 g, 12.1 mmol) dissolved in anhydrous CH$_2$Cl$_2$ (100 mL) under N$_2$ atmosphere. BF3.etherate (0.083 g, 0.67 mmol) was then added to the solution and then the resulting reaction mixture at RT for 1.5 days. The reaction mixture was quenched with a saturated aqueous NaHCO$_3$ solution and extracted with ethyl acetate (200 mL). The organic layer was washed with water (200 mL) and dried with anhydrous Na$_2$SO$_4$. The residue was purified by silica gel column chromatography (EtOAc/hexane) providing a desired product (7) as a white solid (3.3 g, 55%). $^1$H NMR (300 MHz, CDCl$_3$): δ 5.35 (d, J=5.2 Hz, 1H), 4.41 (q, J=7.3 Hz, 1H), 4.20 (q, J=7.0 Hz, 2H), 4.12 (s, 2H), 3.52-3.42 (m, 1H), 3.37 (t, J=10.6 Hz, 1H), 3.28-3.18 (m, 1H), 2.46-2.34 (m, 1H), 2.34-2.18 (m, 1H), 2.07-1.80 (m, 5H), 1.80-1.34 (m, 13H), 1.28 (t, J=7.2 Hz, 3H), 1.30-1.04 (m, 3H), 1.04-0.89 (m, 8H), 0.89-0.72 (m, 6H); $^{13}$C NMR (75 MHz, CDCl$_3$): δ 171.1, 140.8, 124.0, 121.9, 109.5, 81.0, 80.2, 67.0, 66.0, 62.3, 61.0, 56.7, 50.3, 41.8, 40.5, 40.0, 38.9, 37.3, 37.2, 32.3, 32.1, 31.6, 30.5, 29.0, 28.3, 21.0, 19.6, 17.3, 16.5, 14.7, 14.4; MS (MALDI-TOF): calcd. for C$_{31}$H$_{48}$O$_5$ [M+NH$_4$]$^+$ 518.3840. found 518.3837.

Compound 8. This compound was synthesized via the synthetic protocol of compound 3 by using compound 7 as a starting material. Yield: 89%; $^1$H NMR (300 MHz, CDCl$_3$): δ 5.35 (d, J=5.2 Hz, 1H), 4.41 (q, J=7.3 Hz, 1H), 3.72 (t, J=4.6 Hz, 2H), 3.59 (t, J=4.6 Hz, 2H), 3.52-3.42 (m, 1H), 3.37 (t, J=10.6 Hz, 1H), 3.26-3.11 (m, 1H), 2.45-2.31 (m, 1H), 2.26-2.14 (m, 1H), 2.08-1.82 (m, 6H), 1.82-1.37 (m, 12H), 1.37-1.05 (m, 4H), 1.05-0.88 (m, 8H), 0.85-0.69 (m, 6H); $^{13}$C NMR (75 MHz, CDCl$_3$): δ 141.0, 121.7, 109.5, 81.0, 79.6, 69.2, 68.3, 67.0, 62.3, 56.7, 50.3, 41.8, 40.5, 40.0, 37.4, 37.2, 32.3, 32.1, 31.6, 30.5, 29.0, 28.6, 21.1, 19.6, 17.3, 16.5, 14.7; MS (MALDI-TOF): calcd. for C$_{29}$H$_{46}$O$_4$ [M+NH$_4$]$^+$ 476.3735. found 476.3739.

Compound 9. This compound was synthesized via the synthetic protocol of compound 4 by using compound 8 as a starting material. Yield: 86%; $^1$H NMR (300 MHz, CDCl$_3$): δ 5.35 (s, 1H), 4.41 (q, J=7.3 Hz, 1H), 3.78 (t, J=6.8 Hz, 2H), 3.52-3.32 (m, 4H), 3.27-3.15 (m, 1H), 2.42-2.31 (m, 1H), 2.29-2.16 (m, 1H), 2.08-1.81 (m, 5H), 1.81-1.37 (m, 12H), 1.36-1.05 (m, 4H), 1.05-0.92 (7H), 0.92-0.73 (m, 7H); $^{13}$C NMR (75 MHz, CDCl$_3$): δ 140.9, 121.8, 109.5, 81.0, 79.8, 68.3, 67.1, 62.3, 56.7, 50.3, 41.8, 40.5, 40.0, 39.3, 37.4, 37.2, 32.3, 32.1, 31.6, 31.1, 30.5, 29.0, 28.6, 21.1, 19.6, 17.4, 16.5, 14.7; MS (MALDI-TOF): calcd. for $C_{29}H_{45}O_3Br$ $[M+H]^+$ 521.2625. found 521.2621.

Compound 10. This compound was synthesized via the synthetic protocol of compound 6 by using compound 9 as a starting material. Yield (two steps): 90%; $^1$H NMR (300 MHz, CDCl$_3$): δ 5.34 (d, =5.2 Hz, 1H), 4.41 (q, =7.4 Hz, 1H), 3.78-3.63 (m, 4H), 3.57 (t, =5.6 Hz, 2H), 3.52-3.42 (m, 1H), 3.37 (t, =10.6 Hz, 1H), 3.27-3.08 (m, 1H), 2.87 (s, 2 h), 2.45-2.30 (m, 1H), 2.27-2.12 (m, 1H), 2.08-1.34 (m, 21H), 1.34-1.05 (m, 4H), 1.05-0.88 (m, 8H), 0.88-0.72 (m, 7H); $^{13}$C NMR (75 MHz, CDCl$_3$): δ 140.8, 121.8, 109.5, 81.0, 79.6, 67.1, 66.4, 65.4, 62.3, 56.7, 41.8, 50.3, 40.5, 40.1, 39.1, 37.3, 37.2, 32.3, 32.0, 31.6, 30.5, 29.5, 29.0, 28.5, 21.1, 19.6, 17.3, 16.5, 14.7; MS (MALDI-TOF): calcd. for $C_{32}H_{52}O_5$ $[M+Na]^+$ 539.3707. found 539.3714.

GDNa was synthesized according to the general procedure for glycosylation. $^1$H NMR (300 MHz, CDCl$_3$): δ 8.14-7.90 (m, 15H), 7.90-7.83 (m, 4H), 7.83-7.77 (m, 4H), 7.77-7.68 (m, 4H), 7.68-7.15 (m, 42H), 6.13 (t, J=10.0 Hz, 2H), 5.73-5.59 (m, 4H), 5.35 (q, J=9.7 Hz, 2H), 5.29-5.03 (m, 8H), 4.71-4.48 (m, 4H), 4.48-4.14 (m, 9H), 3.69-3.57 (m, 2H), 3.53-3.23 (m, 7H), 3.13-2.92 (m, 4H), 2.85-2.74 (m, 1H), 2.32-2.20 (m, 1H), 2.20-1.81 (m, 5H), 1.80-1.70 (m, 5H), 1.70-1.55 (m, 4H), 1.55-1.40 (m, 4H), 1.40-1.02 (m, 8H), 1.02-0.94 (m, 3H), 0.94-0.83 (m, 6H), 0.83-0.70 (m, 5H); $^{13}$C NMR (75 MHz, CDCl$_3$): δ 166.3, 166.2, 166.0, 165.6, 165.2, 165.1, 165.0, 141.1, 133.7, 133.6, 133.4, 133.3, 130.1, 129.9, 129.8, 129.6, 129.5, 129.3, 129.1, 129.0, 128.9, 128.8, 128.7, 128.6, 128.4, 128.3, 121.3, 109.3, 101.1, 95.8, 81.0, 78.9, 74.7, 72.3, 72.2, 70.0, 69.2, 69.1, 67.0, 62.7, 60.6, 56.7, 50.2, 41.8, 40.4, 40.0, 37.3, 37.1, 32.2, 32.0, 31.6, 30.5, 29.0, 28.5, 21.0, 19.5, 17.3, 16.5, 15.5, 14.7; MS (MALDI-TOF): calcd. for $C_{154}H_{148}O_{39}$ $[M+Na]^+$ 2643.9. found 2644.6.

GDN was synthesized according to the general procedure for de-O-benzoylation. $^1$H NMR (300 MHz, CDCl$_3$): δ 5.37 (d, J=5.2 Hz, 1H), 5.15 (d, J=3.4 Hz, 2H), 4.39 (q, J=7.7 Hz, 1H), 4.10 (d, J=7.6 Hz, 2H) 3.98-3.74 (m, 8H), 3.72-3.54 (m, 12H), 3.54-3.47 (m, 3H), 3.47-3.40 (m, 3H), 3.40-3.32 (m, 2H), 3.32-3.08 (m, 5H), 2.43-2.30 (m, 1H), 2.20-1.82 (m, 3H), 1.82-1.06 (m, 18H), 1.06-1.00 (m, 4H), 0.96 (d, J=6.9 Hz, 4H), 0.85-0.74 (m, 6H)$^{13}$C NMR (75 MHz, CDCl$_3$): δ 142.2, 122.6, 110.7, 104.9, 104.7, 103.1, 82.4, 81.5, 80.6, 78.0, 76.7, 75.2, 75.0, 74.3, 71.7, 70.8, 68.0, 67.2, 63.9, 62.9, 62.4, 58.0, 51.8, 43.1, 41.6, 41.8, 40.4, 38.6, 38.3, 38.0, 33.3, 33.0, 32.9, 32.6, 31.6, 30.0, 29.9, 29.7, 22.2, 20.0, 17.7, 16.9, 15.1; MS (MALDI-TOF): calcd. for $C_{56}H_{92}O_{25}$ $[M+Na]^+$ 1187.5820. found 1187.5769.

Example 3

Protein Stability Evaluation

Bacteriorhodopsin Stability.

The procedure for the bR stability assay generally followed the reported protocol (Bazzacco et al., Biomacromolecules 2009, 10, 3317-3326). Frozen aliquots of purple membranes containing bR at 184 μM were thawed at room temperature and solubilized by using an octylthioglucoside (OTG) solution for 24 hr at 4° C. in a dark room. For this purpose, OTG (CMC=0.28 wt %) was used at 2.0 wt % in 10 mM sodium phosphate (pH 6.9). Membrane debris was then removed from the solubilized material via ultracentrifugation at 200,000 g at 4° C. for 20 min. The supernatant, including bR protein, was transferred into individual DDM, GLC, or GDN solutions, giving final concentration of OTG: new amphiphiles=0.2 wt %: 0.8 wt % (1:4) or 0.2 wt %:1.6 wt % (1:8). The stability of bR in each solution was monitored by measuring absorbance at 554 nm over 20 days.

Solubilization and Stability Assay for R. capsulatus Superassembly.

The solubilization and stability of the R. capsulatus superassembly were assessed according to the published protocol (Chae et al., J. Am. Chem. Soc. 2010, 132, 16750-16752). Briefly, specialized photosynthetic membranes obtained from an engineered strain of Rhodobacter (R.) capsulatus, U43[pUHTM86Bgl], lacking the LHII light-harvesting complex, were used. Solubilization of the LHI-RC superassembly began by thawing, homogenizing, and incubating frozen aliquots of R. capsulatus membranes at 32° C. for 30 min. Subsequent 30-min incubation was performed after adding DDM or LDAO at 1.0 wt % or GDN at 2.0 wt % in the solid form. The solution was then subjected to ultracentrifugation at 315,000 g at 4° C. for 30 min to remove membrane debris. To assess solubilization efficiency, UV-Vis spectra of the solubilized protein solutions were measured in a range of 650~950 nm.

For the stability assay, DDM-solubilized material was transferred into a new microcentrifuge tube containing Ni-NTA resin (Qiagen, Inc.; Valencia, Calif.; pre-equilibrated and stored in an equal volume of buffer containing 10 mM Tris, pH 7.8, and 100 mM NaCl). After a 1 h incubation at 4° C. for binding, the resins were washed twice with 0.5 mL of binding buffer (a pH 7.8 Tris solution containing DDM at 1×CMC) and eluted three times with 0.20 mL elution buffer aliquots containing 1 M imidazole (otherwise, this buffer was identical to binding buffer; the pH of each solution was readjusted to pH=7.8). The DDM-purified solutions were collected and diluted with 0.4 mL of the binding buffer. Then small aliquots (0.05 mL) of the DDM-purified protein solutions were mixed with 0.95 mL GLC or GDN solutions at concentrations CMC+0.04 wt %, CMC+0.2 wt % or CMC+1.0 wt %. UV-Vis spectra of these solutions were monitored at room temperature over 20 days. Protein degradation was assessed by measuring the 875 nm/680 nm absorbance ratio.

Membrane Solubilization and Protein Purification (CMP-Sia, GlpG and SQR).

CMP-Sia and GlpG were expressed as fusion proteins with a C-terminal GFP-His tag in Saccharomyces cerevisiae and Escherichia coli respectively. All steps were carried out at 4° C. Membranes containing CMP-Sia and GlpG were resuspended in PBS, 10 mM imidazole pH 8.0, 150 mM NaCl, 10% glycerol and solubilized in 1% DDM for 1 hour with mild agitation. Supernatant containing DDM-solubilized protein was harvested after ultracentrifugation at 100,000 g for 45 min. The GFP-His fusions, CMP-Sia and GlpG were individually bound to Ni$^{2+}$-NTA resin (1 ml per 1 mg of GFP fusion) pre-equilibrated with Buffer A (PBS, 10 mM Imidazole pH 8.0, 150 mM NaCl, 10% glycerol, 0.03% DDM) using stirred mixing for 2-3 hrs. The resin was washed with 10 CV of Buffer A, then 35 CV of Buffer A supplemented with 30 mM imidazole, followed by elution using 2-3 CV of Buffer A supplemented with 250 mM Imidazole.

Equal amounts of His-tagged TEV protease was added to the GFP-His fusions in the eluate, and the samples dialysed overnight against Buffer B (20 mM Tris (pH 7.5), 150 mM NaCl, 0.03% DDM). Cleaved CMP-Sia and GlpG were isolated in the flowthrough fractions using reverse Ni$^{2+}$-NTA binding. Samples were concentrated to a 0.5 ml volume using centrifugal concentrators, and submitted to a final polishing gel filtration step using a Superdex 200 10/300 column pre-equilibrated with Buffer B. CMP-Sia and GlpG were concentrated to 6 mg/ml and 5 mg/ml respectively, using molecular weight cut-off filters.

SQR was expressed in *E. coli* as an untagged construct. Membranes (~400 mg) containing SQR were resuspended in 20 mM potassium phosphate (pH 7.4), 0.2 M EDTA and solubilized in 2% $C_{12}E_9$ for 15 min. Supernatant containing detergent-solubilized protein was harvested following ultracentrifugation at 100,000 g for 45 min, and filtered through a 0.2 µm filter. SQR was bound to pre-equilibrated Q-sepharose Fast Flow resin in an XK26/20 column (~24 ml). The column was washed with 2 CV of Buffer C (20 mM potassium phosphate (pH 7.4), 0.2 M EDTA, 0.05% $C_{12}E_9$), 2 CV of Buffer C supplemented with 100 mM NaCl, followed by elution using a (100-350) mM NaCl gradient. Fractions containing SQR were concentrated using an Amicon stirred cell concentrator, and filtered. The SQR was then applied onto a Phoros 50 HQ resin using an XK16/20 column (~20 ml) pre-equilibrated with Buffer C, followed by a Sephacryl 300 26/60 pre-equilibrated with buffer D (20 mM potassium phosphate (pH 7.4), 0.05% $C_{12}E_9$). The final buffer exchange was performed on a Superdex 200 10/300 gel filtration column pre-equilibrated with 20 mM Tris (pH 7.6), 0.2% decyl-β-D-maltoside (DM). SQR was concentrated to 12 mg/ml using molecular weight cut-off filters.

Samples for CPM Assay and Gel Filtration Analysis.

CPM dye (Invitrogen), stored in DMSO (Sigma), was diluted (1:100) in Buffer B supplemented with 5 mM EDTA. Test amphiphiles or DDM were used at CMC+0.04 wt % concentrations in 20 mM Tris (pH 7.5), 150 mM NaCl. 1 µl of the purified protein; CMP-Sia (6 mg/ml), GlpG (5 mg/ml) and SQR (12 mg/ml) was individually added to test buffers (150 µl) in Greiner 96-well plates, and left for equilibration at RT for 5 min, before adding 3 µl diluted CPM dye. For gel filtration analysis, 10 µl of purified CMP-Sia (6 mg/ml) was diluted in 1000 µl test buffer. Test buffer (20 mM Tris (pH 7.5), 150 mM NaCl) included DDM or GDN at 0.042 wt % (corresponds to CMC+0.033 wt % for DDM and CMC+ 0.040 wt % for GDN). 500 µl aliquots of the diluted protein were applied onto a Superdex 200 30/100 gel filtration column, before and after incubation at 30° C. for 2 hr. The column was pre-equilibrated with the respective test buffer prior to sample loading.

LeuT Functional Assay.

LeuT activity was measured according to the reported procedure (Chae et al., *J. Am. Chem. Soc.* 2010, 132, 16750-16752). The wild type of the leucine transporter (LeuT) from *Aquifex aeolicus* was expressed in *E. coli* C41(DE3) harboring pET16b encoding LeuT WT-His8, essentially as described by Chae et al. Plasmid was kindly provided by E. Gouaux (Vollum Institute, Portland, Oreg., USA). Briefly, after isolation of bacterial membranes followed by solubilization in 1% DDM, the LeuT was purified by nickel affinity chromatography in 20 mM Tris-HCl (pH 8.0), 1 mM NaCl, 199 mM KCl, 0.05% DDM. Subsequently, approx. 1.5 mg/ml protein stock was diluted ten-fold in same buffer without DDM, but containing GDN, GLC-1, GLC-2 or GLC-3 in final concentrations of CMC+0.04 wt % or CMC+0.2 wt %, respectively. In control samples, DDM was used at the above-mentioned final concentrations. Following protein storage at RT, at the indicated time points, samples were centrifuged and the protein concentration was assessed by determining absorbance at 280 nm. Concomitantly, for the corresponding time points, [$^3$H]-Leu binding was measured using scintillation proximity assay (SPA). Briefly, SPA reaction mixture consisted of 5 µL from the respective protein samples, 20 nM [$^3$H]-Leu and copper chelate (His-Tag) YSi beads (both from PerkinElmer, USA). Binding was assessed in 200 mM NaCl in the presence of tested compounds at the above-mentioned concentrations, and monitored using MicroBeta liquid scintillation counter (PerkinElmer).

$\beta_2$AR-T4L Thermostability.

A receptor fusion protein of T4 lysozyme inserted in the $3^{rd}$ intracellular loop of the $\beta_2AR^4$ was cloned into BestBac baculovirus (Expression Systems, CA) and expressed in Sf9 insect cell cultures. The receptor was solubilized and purified in DDM as previously described (Kobilka, *Anal. Biochem.* 1995, 231, 269-271). Briefly, the receptor was purified in a three step procedure, M1 FLAG antibody affinity chromatography followed by alprenolol-Sepharose chromatography ending in a second M1 chromatography step. The fluorescent inverse agonist carazolol was bound to the receptor on the second M1 resin following extensive washing in buffer (0.1% DDM, 100 mM NaCl, 20 mM HEPES, pH 7.5) containing 30 µM carazolol. The eluted and carazolol-bound receptor was dialyzed against buffer containing 1 µM carazolol to reduce free carazolol concentration. The receptor was spin concentrated to 7 mg/ml (≈140 µM).

For stability measurements the carazolol-bound receptor was diluted below the CMC for DDM by adding 3 µL of the concentrated receptor in a quartz cuvette containing 600 µL buffer (100 mM NaCl, 20 mM HEPES, pH 7.5) with amphiphiles at various concentrations above their CMC. The cuvette was placed in a Spex FluoroMax-3 spectrofluorometer (Jobin Yvon Inc.) under Peltier temperature control. Fluorescence emission from carazolol was obtained following 5 min incubations from 25 to 85° C. in twelve continuous 5° C. increments. Excitation was set at 325 nm, and emission was measured from 335 to 400 nm with an integration time of 0.3 s nm-1 using a bandpass of 1 nm for both excitation and emission. The 341:356 nm peak ratio was calculated and graphed using Microsoft Excel and GraphPad Prism software.

Solubilization and Stability Assay of $\beta_2$AR WT.

A gene encoding amino-terminally FLAG epitope tagged $\beta_2$AR was expressed in Sf9 cells by baculovirus, with no ligand present during culture. Cells were infected at a density of $4 \times 10^6$ cells/mL and then cultured for 48 hours prior to harvesting by centrifugation. Cells were resuspended and lysed by osmotic shock with a low ionic strength buffer (20 mM Tris pH 7.5, 1 mM EDTA). The lysed cells were aliquoted 35 mg per aliquot, then frozen. For extraction tests, 300 µL of solubilization buffer (20 mM HEPES pH 7.5, 100 mM NaCl) containing each amphiphile was added to each aliquot, which was then homogenized by pipet followed by grinding with a glass dounce tissue homogenizer. After two-hour incubation at 4° C., samples were centrifuged at maximum speed in a tabletop microcentrifuge to pellet insoluble material. Supernatant was removed and assayed for protein concentration by DC protein assay (Bio-Rad).

The amount of functional receptor was quantified by incubation for 1 hour with 10 nM 3H dihydroalprenolol. Samples were then separated by gel filtration over G-50 resin and radioactivity was quantified by liquid scintillation. Nonspecific binding was measured in the presence of 10 µM alprenolol. Assays were performed in triplicate at time points indicated. G-50 filtration was performed in buffer containing 20 mM HEPES pH 7.5, 100 mM NaCl, 10-fold CMC of the detergent tested. All binding assays were performed with ice cold buffers.

Solubilization of δ-Opioid Receptor-T4L Fusion (δOR-T4L).

FLAG epitope tagged δOR-T4L was expressed in Sf9 insect cells using baculovirus particles generated by the pFastBac vector system (Invitrogen). Insect cells were infected and cultured as for the β$_2$AR and cells were lysed by osmotic shock as done for cells expressing β$_2$AR. Lysed cells were used for extraction tests by adding 40 mg of cells to 200 μL of solubilization buffer (20 mM HEPES pH 7.5, 100 mM NaCl) containing each amphiphile. Cell membranes were homogenized in solubilization buffer by 20 passes through a narrow bore needle coupled to a 1 ml syringe. Solubilization reactions were then incubated at 4° C. for two hours and then centrifuged at maximum speed in a tabletop microcentrifuge. The amount of functional receptor after solubilization was quantified by incubation for 1 hour with 10 nM 3H diprenorphine. Binding assays using gel-filtration were carried out as for β$_2$AR, with the exception that 10 μM naloxone was used to determine nonspecific binding.

Solubilization and Thermostability Assay of MelB.

The reported protocol3 was used to evaluate MelB stability with DDM and GDN. Vector pK35ΔAHB/WT MelB/CH$_6$ encoding the wild-type MelB with a 6-His tag at the C-terminus and E. coli DW2-R cells (ΔmelB and ΔlacZY) are used for the assay. Cells were harvested, resuspended in a buffer containing 20 mM Tris, pH 7.5, 200 mM NaCl and 10% glycerol. The harvested cells were subjected to French press and centrifugation at 20,000 g for 15 min. Subsequently, membranes were obtained via ultracentrifugation at 43,000 rpm for 3 hr in the Beckman rotor, Type 45 Ti rotor. A protein assay was carried out with a BCA kit (Thermo Scientific, Rockford, Ill.). For the measurement of solubilization efficiency, membrane samples containing MelB were incubated with a solubilization buffer (20 mM Tris, 200 mM NaCl, 10% glycerol, 20 mM melibiose, pH, 7.5) and 1.5 wt % DDM or GDN at 0° C. for 10 min. The final protein concentration was 10 mg/mL. For the MelB thermostability, the samples were incubated for 90 min at the four different temperatures (0, 45, 55, and 65° C.). After ultracentrifugation at 355,590 g in a Beckman Optima™ MAX Ultracentrifuge using a TLA-100 rotor for 45 min at 4° C., 10 μg protein before and after spin for each condition was analyzed by SDS-12% PAGE and immunoblotted with Penta-His-HRP antibody (Qiagen, Germantown, Md.).

CMP-Sia Solubilization.

CMP-Sia was expressed as a fusion protein with a C-terminal GFP in FGY217 Saccharomyces cerevisiae cells. Cell lysis was conducted by using a cell disrupter (Constant Systems) and the protein samples were subjected to centrifugation at 15,000 g for 10 mins to remove unbroken cells and debris. Subsequently, the membranes were harvested by ultracentrifugation at 150,000 g for 45 min. The membranes were resuspended in 50 mM Tris-HCl (pH 7.6), 1 mM EDTA, 0.6 M sorbitol and the protein concentration was estimated using a BCA kit (Pierce). The membranes were incubated with OG or DDM at 1.0%, or GDN at 2.0% for 1 hr at 4° C. A fluorescence value was measured for each sample before and after ultracentrifugation at 150,000 g for 1 h. The solubilization efficiency was calculated via the fluorescence measurements of the soluble supernatant/the total sample.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of Formula I:

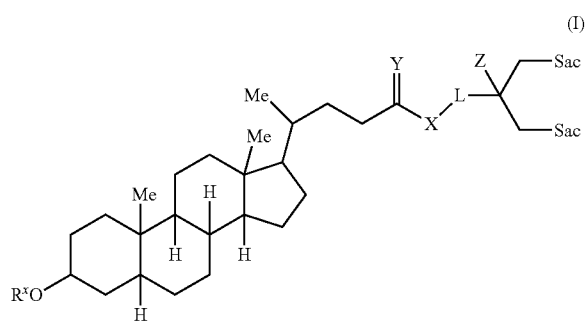

wherein
L is —(CH$_2$)$_n$— where n is 1-12, or a direct bond;
X is NH, O, or a direct bond;
Y is O or absent;
Z is H, methyl, ethyl, propyl, or butyl;
R$^x$ is H, (C$_1$-C$_{24}$)alkyl, aryl, or aroyl; and
each Sac is independently an oxygen-linked monosaccharide, disaccharide, or trisaccharide.

2. The compound of claim 1, wherein R$^x$ is methyl.

3. The compound of claim 1, wherein each Sac is an oxygen-linked monosaccharide.

4. The compound of claim 1, wherein each Sac is an oxygen-linked disaccharide.

5. The compound of claim 1, wherein each Sac is an oxygen-linked trisaccharide.

6. The compound of claim 1, wherein X is NH, Y is O, Z is H, and L is a direct bond.

7. The compound of claim 1, wherein L is —CH$_2$—, X is O, Y is absent, and Z is Me.

8. The compound of claim 1, wherein L is a direct bond, X is a direct bond, Y is absent, and Z is H.

9. The compound of claim 1, wherein the compound is a compound of Formula II, III, or IV:

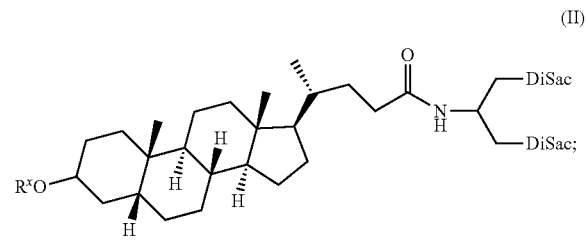

-continued

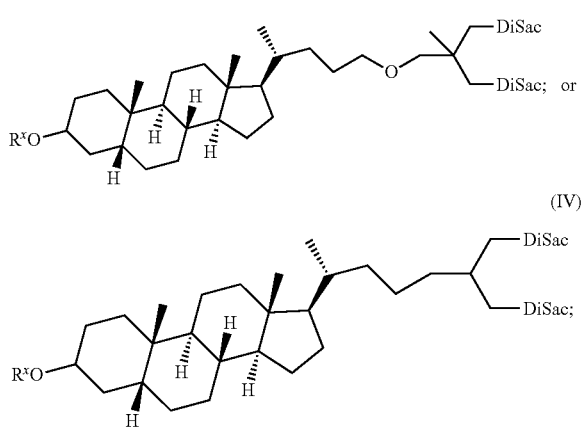

wherein DiSac is an oxygen-linked disaccharide.

10. The compound of claim 9, wherein the compound is:

11. The compound of claim 1, wherein the critical micelle concentration (CMC) of the compound in water is about 5 nM to about 100 nM.

12. The compound of claim 1, wherein a plurality of the compounds form a micelle in water comprising about 5 to about 35 molecules of the compound.

13. A composition comprising a compound of claim 1 and an isolated membrane protein.

14. A micelle comprising a compound of claim 1.

15. The micelle of claim 14, further comprising a polypeptide or a protein.

16. A method of solubilizing or stabilizing a membrane protein comprising contacting a membrane protein with an effective amount of a compound as described by claim 1, in an aqueous solution, and optionally heating the protein and the compound, thereby forming a solubilized or stabilized aggregation or micelle.

17. The method of claim 16, comprising heating the protein and the compound, thereby forming a micelle.

18. A method of extracting a protein from a lipid bilayer comprising contacting the lipid bilayer with an effective

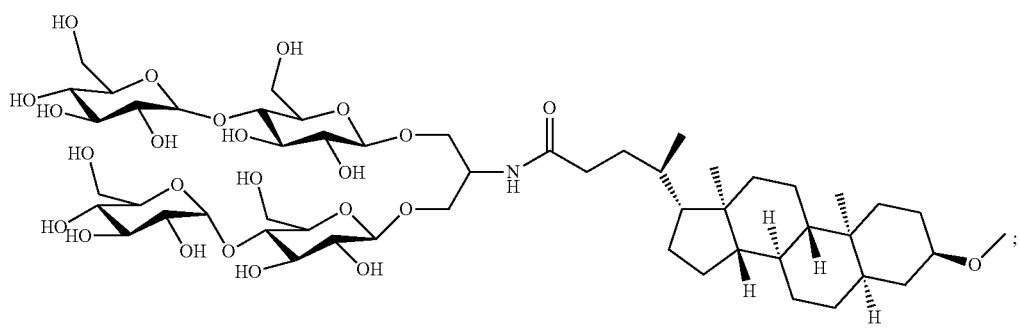

(GLC-1)

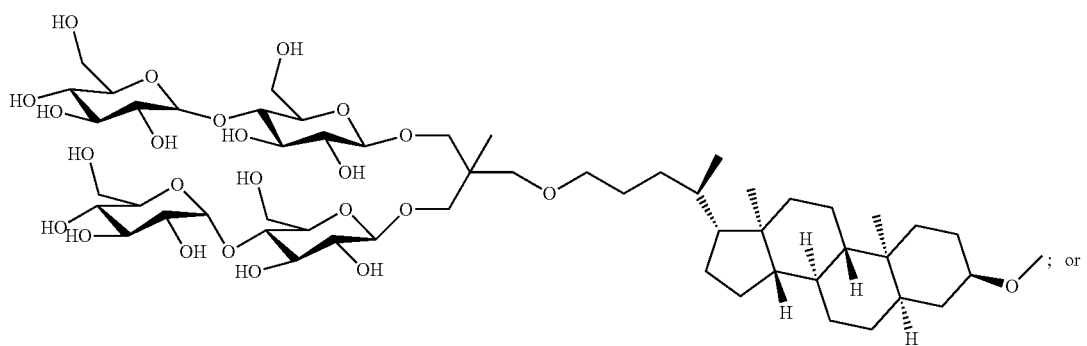

(GLC-2)

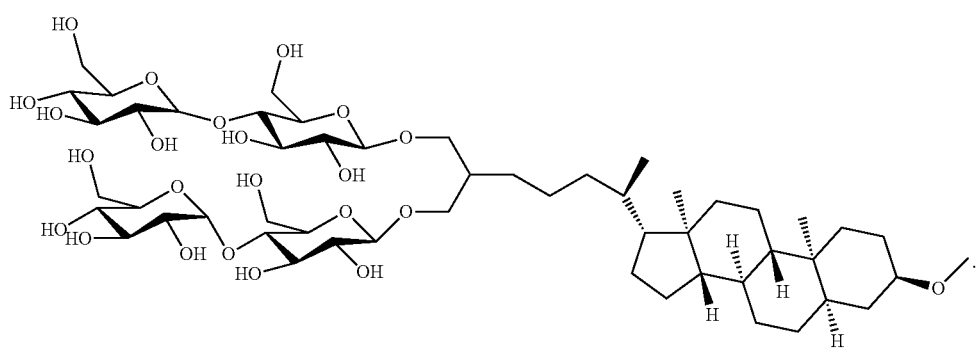

(GLC-3)

amount of a compound of claim 1 in an aqueous solution to form a mixture, optionally in the presence of a buffer, thereby forming an aggregation of the compound and the membrane protein extracted from the lipid bilayer, and separating the aggregation from the mixture.

* * * * *